(12) United States Patent
Omi et al.

(10) Patent No.: US 9,599,608 B2
(45) Date of Patent: Mar. 21, 2017

(54) ANTIBODY AGAINST AFFINITY COMPLEX

(75) Inventors: Kazuya Omi, Tokyo (JP); Tsuyoshi Ando, Tokyo (JP); Yoshiaki Uchida, Tokyo (JP); Katsutoshi Goishi, Tokyo (JP); Yoshie Goishi, legal representative, Tokyo (JP); Asako Oka, Tokyo (JP); Takashi Shirakawa, Tokyo (JP); Takuya Sakyu, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 0 days.

(21) Appl. No.: 14/346,615

(22) PCT Filed: Jul. 4, 2012

(86) PCT No.: PCT/JP2012/067062
§ 371 (c)(1),
(2), (4) Date: Aug. 18, 2014

(87) PCT Pub. No.: WO2013/042426
PCT Pub. Date: Mar. 28, 2013

(65) Prior Publication Data
US 2015/0037813 A1   Feb. 5, 2015

(30) Foreign Application Priority Data

Sep. 21, 2011 (JP) ................. 2011-206162
Jan. 16, 2012 (JP) ................. 2012-006359

(51) Int. Cl.
*C07K 16/44* (2006.01)
*C07K 16/26* (2006.01)
(Continued)

(52) U.S. Cl.
CPC ....... *G01N 33/54306* (2013.01); *C07K 16/26* (2013.01); *C07K 16/44* (2013.01);
(Continued)

(58) Field of Classification Search
CPC .. G01N 33/54306; G01N 33/78; G01N 33/82; G01N 33/743; C07K 16/44;
(Continued)

(56) References Cited

U.S. PATENT DOCUMENTS 4,544,640 A * 10/1985 Soma et al. ................ 436/506
4,840,895 A    6/1989 Self
(Continued)

FOREIGN PATENT DOCUMENTS

CN    1671842 A    7/2003
JP    61-501657    8/1986
(Continued)

OTHER PUBLICATIONS

Campos et al., Molecular Mechanisms of Microcystin Toxicity in Animal Cells, International Journal of Molecular Sciences 2010, 11, pp. 268-287.*

(Continued)

*Primary Examiner* — Shafiqul Haq
(74) *Attorney, Agent, or Firm* — Oblon, McClelland, Maier & Neustadt, L.L.P.

(57) ABSTRACT

The present invention provides a means and a method for specifically measuring a substance such as a small substance with high sensitivity by a sandwich method. Specifically, the present invention provides an antibody capable of specifically binding to an affinity complex and a method of measuring of the affinity complex comprising measuring the affinity complex using the antibody capable of specifically binding to the affinity complex. The antibody of the present invention may be a full-length antibody. The antibody of the present invention may also have a region derived from an immunoglobulin from an animal having an ability of gene conversion (e.g., a complementarity-determining region, a framework region, or a variable region). Examples of at least (Continued)

one factor that constitutes the affinity complex include a small substance or a protein (e.g., antibody).

4 Claims, 12 Drawing Sheets

(51) Int. Cl.
*G01N 33/543* (2006.01)
*G01N 33/531* (2006.01)
*G01N 33/74* (2006.01)
*G01N 33/78* (2006.01)
*G01N 33/82* (2006.01)

(52) U.S. Cl.
CPC ......... *G01N 33/531* (2013.01); *G01N 33/743* (2013.01); *G01N 33/78* (2013.01); *G01N 33/82* (2013.01); *C07K 2317/24* (2013.01); *C07K 2317/32* (2013.01); *C07K 2317/92* (2013.01)

(58) Field of Classification Search
CPC  C07K 16/26; C07K 2317/32; C07K 2317/24; C07K 2317/92
See application file for complete search history.

(56) References Cited

U.S. PATENT DOCUMENTS

| | | | |
|---|---|---|---|
| 5,187,065 A * | 2/1993 | Schutzer | 435/7.32 |
| 5,223,441 A | 6/1993 | Ullman et al. | |
| 5,807,715 A * | 9/1998 | Morrison et al. | 435/69.6 |
| 2006/0183225 A1 | 8/2006 | Ohta et al. | |
| 2006/0246506 A1 | 11/2006 | Pulli et al. | |
| 2010/0203560 A1 | 8/2010 | Tamm et al. | |

FOREIGN PATENT DOCUMENTS

| | | |
|---|---|---|
| JP | 63-112599 A | 5/1988 |
| JP | 2001-174460 | 6/2001 |
| JP | 2006-506634 | 2/2006 |
| JP | 2006-282521 | 10/2006 |
| JP | 2010-523994 | 7/2010 |
| WO | WO 85/04422 | 10/1985 |
| WO | 2004/011644 | 2/2004 |

OTHER PUBLICATIONS

Monnet et al., Highly Specific Anti-estradiol antibody: Structural Characterization and Binding Diversity, J. Mol. Biol. 2002, 315, pp. 699-712.*
Magari et al., Enhancement of antibody production from a chicken B cell line DT40 by reducing Pax5 expression, Journal of Bioscience and Bioengineering, vol. 107, No. 2, 2009, pp. 206-209.*
Magari et al., Enhancement of hypermutation frequency in the chicken B cell line DT40 for efficient diversification of the antibody repertoire, Biochemical and Biophysical Communications 396, 2010, pp. 353-358.*
Papanastasiou-Diamandi et al. Immunoassay of triiodothyronine in serum by time-resolved fluorometric measurement of europium-chelate complexes in solution. CLinical Biochemistry 1992, pp. 255-261. two pages of Abstract provided.*
Seo et al. Rapid generation of specific antibodies by enhanced homologous recombination. Nature Biotechnology 2005, vol. 23, No. 6, pp. 731-735.*
Combined Chinese Office Action and Search Report issued Sep. 25, 2015 in Patent Application No. 201280045570.1 (with English Translation), English portions only.
Hong Zhang et al., "The Relationship Between Chicken Immunoglobulin Gene Structure and Antibody Diversity Production Molecular Mechanism", Journal of Henan Agricultural Sciences, Feb. 15, 2007, pp. 102-105, English portion only for Zhang.
U.S. Appl. No. 14/762,263, filed Jul. 21, 2015, Uchida, et al.
Office Action dated Apr. 8, 2016., issued in corresponding EP Patent application No. 12 833 103.0, (Fujirebio Inc.), 8 pp.
Waka Lin, et al., "B-cell display-based one-step method to generate chimeric human IgG monoclonal antibodies", Nucleic Acids Research, 2011, vol. 39, No. 3, 10 pp., (Foreigh copy and English translation).
Jian-Min Chen, et al., "Gene conversion: mechanisims, evolution and human disease", Oct. 2007, vol. 8, www.nature.com/reviews/genetics 762-775., (Foreigh copy and English translation).
Office Action issued on Feb. 18, 2016 in corresponding Russian Patent Application No. 2014115676/10, with English translation, 9 pp. (Foreigh copy and English translation).
Roitt, I., Brostoff J., Male D., "Immunology", translation from English- M: Mir, 2000, p. 110., 5 pp.
"Immunology", in 3 volumes, edited by Paul W., translation from English., M.: Mir, 1987-1989, vol. 1, pp. 243-248, 20 pp. (Foreigh copy and English translation).
Yarilin, A.A., "Fundamentals of Immunology", M.: Medicine, 1999, pp. 172-174, 10 pp. (Foreigh copy and English translation).
Office Action issued in corresponding Taiwanese Patent Application No. 10520290210, dated Mar. 10, 2016, 5pp.
International Search Report Issued Oct. 2, 2012 PCT/JP12/067062 filed Jul. 4, 2012.
Rossotti, M. A. et al., "Phage Anti-Immunocomplex Assay for Clomazone: Two-Site Recognition Increasing Assay Specificity and Facilitating Adaptation into an On-Site Format", Anal. Chem., vol. 82, No. 21, pp. 8838-8843, 2010.
Ihara, M. et al., "Open-sandwich Enzyme Immunoassay for One-Step Noncompetitive Detection of Corticosteroid 11-Deoxycortisol", Anal. Chem., vol. 81, No. 20, pp. 8298-8304, 2009.
Ullman, Edwin F. et al., "Anti-immune complex antibodies enhance affinity and specificity of primary antibodies", Proc. Natl. Acad. Sci., vol. 90, pp. 1184-1189, 1993.
Tamm, Natalia N. et al., "Novel Immunoassay for Quantification of Brain Natriuretic Peptide and Its Precursor in Human Blood", Clinical Chemistry., vol. 54, No. 9, pp. 1511-1518, 2008.
Oguri, H.et al., "Synthesis-Based Approach toward Direct Sandwich Immunoassay for Ciguatoxin CTX3C", J. Am. Chem. Soc., vol. 125, No. 125, pp. 7608-7612, 2003.
Self, Colin H. et al., "High-Performance Assays of Small Molecules: Enhanced Sensitivity, Rapidity, and Convenience Demonstrated with a Noncompetitive Immunometric Anti-Immune Complex Assay System for Digoxin", Clinical Chemistry, vol. 40, No. 11, pp. 2035-2041, 1994.
Foreign Office Action issued Nov. 28, 2016 in corr. Japanese Patent Application No. 2013-534624 (with English machine translation).
Ohta et al., "ADLib System for Rapid and Flexible Design of Monoclonal Antibodies", Yakugaku Zasshi (Journal of the Pharmaceutical Society of Japan), vol. 127. No. 1, 2007, pp. 81-89.

* cited by examiner

ANTIBODY AGAINST AFFINITY COMPLEX

TECHNICAL FIELD

The present invention relates to an antibody against an affinity complex, and an assay for a factor that constitutes the affinity complex using the antibody against the affinity complex, and the like.

BACKGROUND ART

Currently, quantification of small substances such as hormones, pharmaceuticals and peptides using an immunoassay is performed frequently. When a substance to be measured is a small substance, a quantification method referred to as a competitive inhibition method is used.

A measurement sensitivity in the competitive inhibition method depends on an affinity of an antibody to be used for an antigen, and generally when an antibody is raised against a small substance, it is known that it is difficult to obtain an antibody with high affinity. Also in the competitive inhibition method, specificity of an antibody is exerted based on reactivity of a type of antibody, and thus, it is necessary to acquire an antibody with high specificity, but it is difficult to acquire such an antibody. That is, a huge amount of effort is required for selecting an antibody that satisfies the sensitivity of the measurement and the specificity upon the measurement by the competitive inhibition method. Even if such an antibody can be selected fortunately, the competitive inhibition method is disadvantageous in that measurement accuracy and the measurement sensitivity are low and it is complicated to determine a competitive condition between a sample and a labeled antigen when a concentration of a substance to be measured is high or low.

The above disadvantage in the competitive inhibition method can be solved by a sandwich method of measuring using two antibodies that recognize different epitopes of an antigen. However, in the case of a small substance, there is only one epitope, and steric hindrance occurs between two antibodies. Thus, it is thought to be difficult to quantify the small substance using the common sandwich method.

A measurement method using an antibody that recognizes an antigen/antibody complex has been reported as a method for measuring a small substance using the sandwich method. In vivo methods using an animal (e.g., hybridoma methods) and in vitro methods (e.g., phage display methods) are known as methods of producing an antibody. For example, in Nonpatent Literature 1, it has been described that an antibody against a low molecular hapten (Δ9-tetrahydrocannabinol: MW 314.5)/antibody complex was successfully obtained by a mouse immunization method, and about 200 clones for the anti-mouse antibody (idiotype) antibody were established by repeating a fusion experiment 5 times, but only one clone was obtained as the antibody recognizing the complex.

Methods disclosed in Patent Literatures 1 and 2 and Nonpatent Literatures 1 to 4 are known as to methods of measuring a small substance by the sandwich methods.

Methods disclosed in Patent Literature 3 are known as to technologies of producing an antibody and antibody-producing cells.

PRIOR ART REFERENCES

Patent Literatures

Patent literature 1: International Publication WO2008/125733

Patent literature 2: JP 2001-174460 A
Patent literature 3: International Publication WO2004/011644

Non-Patent Literatures

Non-Patent Literature 1: Ulman et al., Proc. Natl. Acad. Sci. U.S.A., 90, 1184-89 (1993)
Non-Patent Literature 2: Tamm at al., Clinical Chemistry, (9), 1511-1518 (2008)
Non-Patent Literature 3: Oguri et al., Journal of American Chemical Society, 125 (25), 7608-7612 (2003)
Non-Patent Literature 4: Self et al., Clinical Chemistry, 40 (11), 2035-2041 (1994)
Non-Patent Literature 5: Rossotti et al., Anal. Chem., 82, 8838-8843 (2010)

DISCLOSURE OF INVENTION

Problem to be Solved by the Invention

It is an object of the present invention to measure a substance such as a small substance specifically with high sensitivity by a sandwich method.

Means for Solving Problem

As a result of an extensive study, the present inventors have succeeded in obtaining a good antibody capable of specifically binding to an affinity complex (e.g., a complex comprising a small substance and an antibody thereto) by using the affinity complex and a given method in combination, as well as in measuring a factor that constitutes the affinity complex (e.g., a substance such as the small substance) specifically with high sensitivity by a sandwich method using such an antibody, and have completed the present invention.

That is, the present invention is as follows.
[1] An antibody capable of specifically binding to an affinity complex.
[2] The antibody according to [1], wherein the antibody is a full-length antibody.
[3] The antibody according to [1], wherein the antibody has a region derived from an immunoglobulin from an animal having an ability of gene conversion.
[4] The antibody according to [3], wherein the region derived from the immunoglobulin from the animal having the ability of gene conversion is a complementarity-determining region, a framework region, or a variable region.
[5] The antibody according to any of [1]-[4], wherein at least one factor that constitutes the affinity complex is a small substance.
[6] The antibody according to any of [1]-[5], wherein at least one factor that constitutes the affinity complex is a protein.
[7] The antibody according to any of [1]-[6], wherein the affinity complex is a complex comprising a small substance and an antibody thereto.
[8] The antibody according to [7], wherein the small substance is (a) a steroid compound, (b) an amino acid compound, or (c) a vitamin.
[9] The antibody according to [8], which is any of the following (a) to (c):
(a) the steroid compound is an estrogen;
(b) the amino acid compound is a thyroid hormone; or
(c) the vitamin is a vitamin D.

[10] The antibody according to [9], which is any of the following (a) to (c):
(a) the estrogen is estradiol;
(b) the thyroid hormone is triiodothyronine; or
(c) the vitamin D is 25OH vitamin D3 or 25OH vitamin D2.
[11] The antibody according to [10], which exhibits a binding rate of the following (a) to (c):
(a) when a binding rate of an antibody (antibody I) capable of specifically binding to an affinity complex comprising the estradiol and an anti-estradiol antibody (affinity complex I) to the affinity complex I is calculated as 100%, a binding rate of the antibody I to an affinity complex comprising estrone and the anti-estradiol antibody (affinity complex I'), an affinity complex comprising estriol and the anti-estradiol antibody (affinity complex I"), an affinity complex comprising an estradiol conjugate and the anti-estradiol antibody (affinity complex I'''), an affinity complex comprising estramustine and the anti-estradiol antibody (affinity complex I""), or an affinity complex comprising estromustine and the anti-estradiol antibody (affinity complex I""') is 10% or less;
(b) when a binding rate of an antibody (antibody II) capable of specifically binding to an affinity complex comprising the triiodothyronine and an anti-triiodothyronine antibody (affinity complex II) to the affinity complex II is calculated as 100%, a binding rate of the antibody II to an affinity complex comprising diiodothyronine and the anti-triiodothyronine antibody (affinity complex II') or an affinity complex comprising thyroxine and the anti-triiodothyronine antibody (affinity complex II") is 10% or less; or
(c) when a binding rate of an antibody (antibody III) capable of specifically binding to an affinity complex comprising 25OH vitamin D3 and an anti-25OH vitamin D3 antibody (affinity complex III-1) or an affinity complex comprising 25OH vitamin D2 and an anti-25OH vitamin D2 antibody (affinity complex III-2) to the affinity complex III-1 or III-2 is calculated as 100%, a binding rate of the antibody III to an affinity complex comprising 1,25(OH)$_2$ vitamin D3 and the anti-25OH vitamin D3 antibody or the anti-25OH vitamin D2 antibody (affinity complex III') or an affinity complex comprising 1,25(OH)$_2$ vitamin D2 and the anti-25OH vitamin D3 antibody or the anti-25OH vitamin D2 antibody (affinity complex III") is 10% or less.
[12] The antibody according to any of [1] to [11], which is produced by a method comprising culturing an antibody-producing cell having an ability to produce the antibody capable of specifically binding to the affinity complex, to give the antibody capable of specifically binding to the affinity complex.
[13] A set, comprising:
(i) an antibody capable of specifically binding to an affinity complex; and
(ii) at least one factor that constitutes the affinity complex.
[14] The set according to [13], which is the following:
(i') an antibody capable of specifically binding to an affinity complex comprising a small substance or a protein and an antibody thereto, and
(ii') an antibody capable of specifically binding to the small substance or the protein.
[15] A method of measuring an affinity complex, comprising measuring the affinity complex using an antibody capable of specifically binding to the affinity complex.
[16] The method according to [15], wherein the affinity complex is measured by a sandwich method.

Effect of the Invention

According to the present invention, the antibody capable of specifically binding to the affinity complex such as an antigen (e.g., small substance)/antibody complex is provided.

According to the present invention, the small substance conventionally measured by the competitive inhibition method can be measured by the sandwich method. According to the measurement by the sandwich method, it is expected to increase a measurement sensitivity, enhance a specificity, improve a measurement accuracy, rapidly construct a measurement system, or the like. Cost down and speed up of the manipulation are easy by automated manipulation because the manipulation for acquiring the antibody is simple.

The present invention is useful for not only the measurement of the small substance but also the measurement of factors other than the small substance and development of pharmaceuticals therapeutically targeting a given factor.

Figure 1:
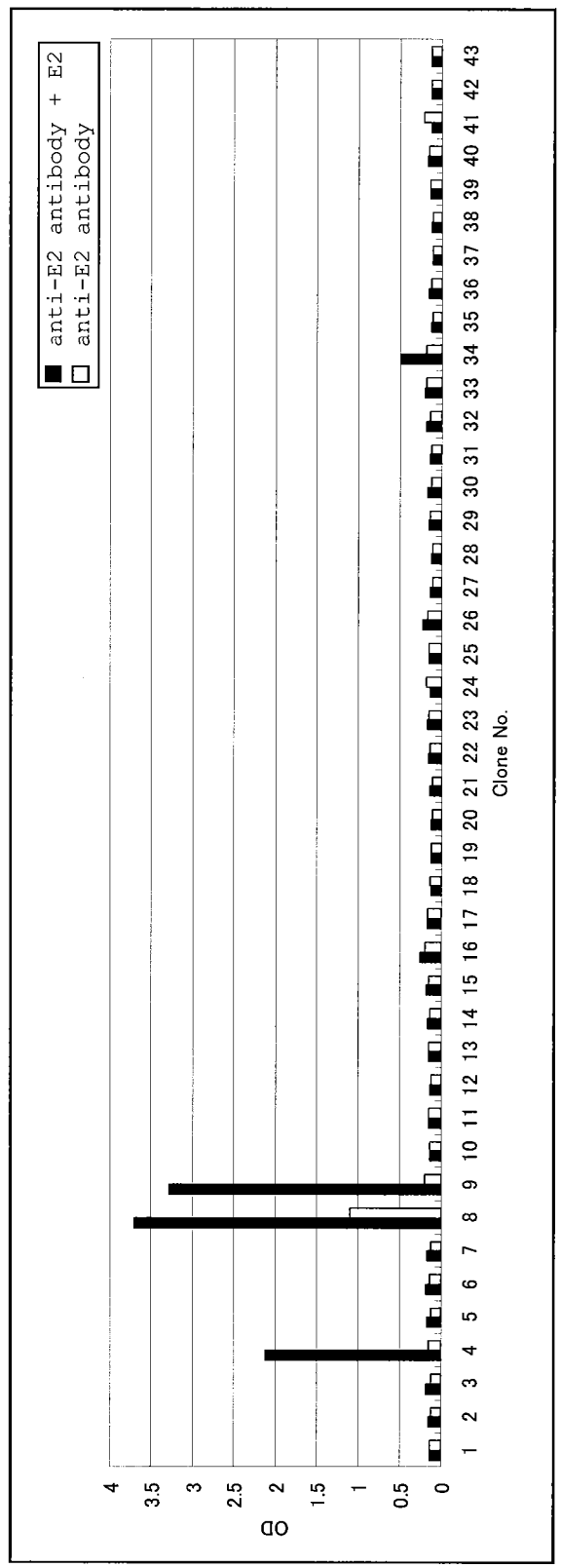
FIG. 1 is a view showing cell clones (No. 1 to 43) obtained by the method of the present invention. Two types of cell clones produced an antibody capable of specifically binding to an antigen/antibody complex (affinity complex comprising estrogen and an anti-estrogen antibody)

MODES FOR CARRYING OUT THE INVENTION (1. Antibody)

The present invention provides an antibody capable of specifically binding to an affinity complex.

The term "affinity complex" refers to a complex formed by association or aggregation (i.e., non-covalent bond) of two or more factors. On the other hand, a complex that is different from the affinity complex includes a covalent complex. The term "covalent complex" refers to a complex formed by a covalent bond between two or more factors. Examples of such a covalent complex include a conjugate obtained by binding a non-immunogenic small substance (i.e., hapten) to a carrier (e.g., protein such as BSA or KLH) via the covalent bond. In other words, the covalent complex can be a complex to be immunized (i.e., immune complex), which has been conventionally administered to an animal in order to elicit an immunity against a non-immunogenic small substance (i.e., hapten) in the animal thereby acquiring an antibody against the small substance. Conventionally, the antibody against the small substance has been produced using such a covalent complex, but it is thought that an antibody capable of specifically binding to the covalent complex (antibody that recognizes a vicinity of a covalent bond portion) is also obtained as a byproduct. However, the antibody against the covalent complex, which is produced using such a conjugate as an antigen, is different from the antibody of the present invention, which is produced using the affinity complex itself as an antigen. A reason for this is, for example, that a steric structure of the covalent complex produced by artificially introducing the covalent bond portion is different from that of the affinity complex formed by a natural association (i.e., non-covalent bond) due to the presence and a location of the covalent bond portion, a potential change of the steric structure (e.g., folding and/or conformation) attributed to the introduction of the covalent bond portion, and the like.

The affinity complex is a homogeneous complex where homogeneous factors are associated or aggregated, or a heterogeneous complex where heterogeneous factors are associated or aggregated. The affinity complex may also be a naturally occurring affinity complex or a non-naturally occurring and artificially produced affinity complex. Examples of the naturally occurring affinity complex include affinity complexes found in viruses and organisms (e.g., microorganisms, insects, plants and animals) and affinity complexes that can be present in environments. The affinity complex is further a multimer (e.g., dimer, trimer, or tetramer). Examples of factors that constitute the affinity complex include proteins, small substances, sugars, nucleic acids (e.g., DNA, RNA), metals, and derivatives thereof.

A factor that constitutes an affinity complex may preferably be a protein. Such a protein include proteins having an ability of an affinity bond and proteins having an aggregation ability. Examples of the protein having the ability of the affinity bond include ligand-dependent proteins [e.g., receptors on a cell membrane such as G protein conjugated receptors, soluble receptors (e.g., immunoglobulin, extracellular domain cleaved from the receptor on the cell membrane), and intranuclear receptors], nucleic acid-binding proteins (e.g., transcription factors, protection or transport proteins for nucleic acids), proteins that form a protein complex (e.g., adaptor proteins), extracellular matrix proteins (e.g., intercellular adhesion proteins), enzymes [e.g., kinases such as tyrosine kinase (receptors or non-receptors), serine/threonine kinase], and glycoproteins. Example of the protein having the aggregation ability include denatured proteins and pathogenic proteins (e.g., neurodegenerative proteins such as β-amyloid).

A protein that is a factor that constitutes an affinity complex may preferably be an antibody. Examples of the antibody that constitutes the affinity complex may be of any isotypes such as IgG, IgM, IgA, IgD, IgE, IgY, and the like. Such an antibody may also be a polyclonal antibody or a monoclonal antibody (e.g., chimera antibody, humanized antibody, human antibody). The antibody that constitutes the affinity complex may be an antibody against an autologous antigen. Such an antibody may also be a full-length antibody or an antibody fragment as described hereinafter. Examples of the antibody fragment may include $F(ab')_2$, Fab', Fab, Fv, and a single chain antibody.

The factor that constitutes the affinity complex may also be preferably a small substance. The term "small substance" refers to a compound having a molecular weight of less than 1,500. The small substance is a natural substance or a synthesized substance. The molecular weight of the small substance may be less than 1,200, less than 1,000, less than 800, less than 700, less than 600, less than 500, less than 400, or less than 300. The molecular weight of the small substance may also be 50 or more, 100 or more, 150 or more, or 200 or more. Examples of the small substance include ligands, hormones, lipids, fatty acids, vitamins, opioids, neurotransmitters (e.g., catechol amine), nucleosides, nucleotides, oligonucleotides, monosaccharides, oligosaccharides, amino acids, and oligopeptides, or pharmaceuticals, toxins and metabolites. Examples of the hormone include steroid hormones, thyroid hormones, and peptide hormones.

In one embodiment, the small substance may be a steroid compound. The steroid compound refers to a compound having a steroid backbone (cyclopentanoperhydrophenanthrene backbone). The steroid compound include steroid hormones, and derivatives thereof having the steroid backbone (e.g., synthesized steroids such as protein anabolic steroid, anti-androgen agents and anti-estrogen agents). Examples of the steroid hormone include androgens, estrogens, progesterones, and corticoids (e.g., glucocorticoid and mineralocorticoid), and the estrogen is preferred. Examples of the estrogen include estrone, estradiol, and estriol. The small substance may also be a metabolite of the steroid compound. Examples of the metabolite of the steroid compound include compounds obtained by adding a hydroxyl group(s) to the steroid compounds as described above, and conjugates. Examples of the conjugate include glucuronic acid conjugates, sulfuric acid conjugates (e.g., compounds in which a sulfate group is conjugated to a hydroxyl group at either position 3 or 17 or to hydroxyl groups at both positions 3 and 17 of estradiol), glutathione conjugates, acetyl conjugates, and amino acid conjugates. In addition, the small substance may also be a steroid compound-like therapeutic drug (e.g., estramustine) or a metabolite thereof (e.g., estromustine).

[Chemical 1]

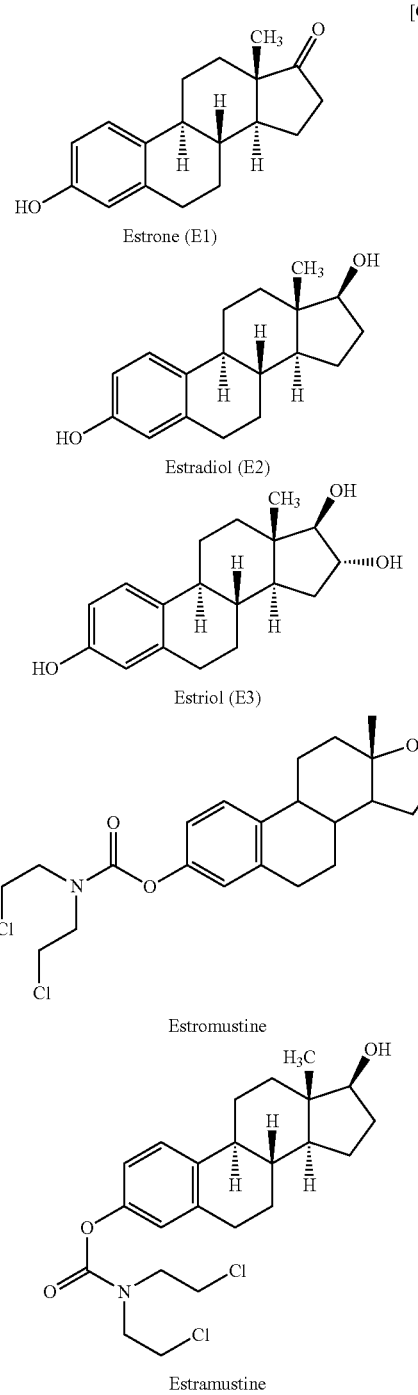

Estrone (E1)

Estradiol (E2)

Estriol (E3)

Estromustine

Estramustine

In another embodiment, the small substance may be an amino acid compound. The amino acid compound refers to a compound having an amino group and a carboxyl group. Examples of the amino acid compound include α-amino acids (e.g., glycine, alanine, asparagine, cysteine, glutamine, isoleucine, leucine, methionine, phenylalanine, proline, serine, threonine, tryptophan, tyrosine, valine, aspartic acid, glutamic acid, arginine, histidine, lysine, ornithine, citrulline), β-amino acids (e.g., β-alanine), γ-amino acids (e.g., γ-aminobutyric acid), as well as derivatives thereof having the amino group and the carboxyl group. The amino acid compound may be an L-isomer or a D-isomer. The small substance may also be a metabolite of the amino acid compound. Examples of the metabolite of the amino acid compound include compounds in which a hydroxyl group is added to the amino acid compound described above, and conjugates as described above. The small substance may further be an amino acid compound-like therapeutic drug or a metabolite thereof.

Preferably, the amino acid compound may be a compound represented by a formula (I): R—$CH_2CH(NH_2)COOH$. R includes the followings:
(i) hydrocarbon group;
(ii) aryl group;
(iii) hydrocarbon-aryl group;
(iv) aryl-hydrocarbon group;
(v) hydrocarbonoxy-hydrocarbon group, aryloxy-hydrocarbon group, hydrocarbonoxy-aryl group, or aryloxy-aryl group;
(vi) hydrocarbonthio-hydrocarbon group, arylthio-hydrocarbon group, hydrocarbonthio-aryl group, or arylthio-aryl group; and
(vii) mono- or di-(hydrocarbon)amino-hydrocarbon group, mono- or di-(aryl)amino-hydrocarbon group, mono- or di-(hydrocarbon)amino-aryl group, or mono- or di-(aryl) amino-aryl group.

The hydrocarbon group is a straight, branched or cyclic non-aromatic hydrocarbon group, and has 1 to 15, preferably 1 to 12, more preferably 1 to 9, and particularly preferably 1 to 6 carbon atoms. Examples of such a hydrocarbon group include alkyl groups (e.g., methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl), alkenyl groups (e.g., ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl), alkynyl groups (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl), and cycloalkyl groups (e.g., cyclopropyl, cyclobutyl, cyclopentyl, cyclohexyl). Examples of hydrocarbon are the same as those of the hydrocarbon group.

The aryl group is an aromatic hydrocarbon group and has, for example, 1 to 14 carbon atoms. Examples of the aryl group include phenyl, naphthyl, anthracenyl, and biphenyl groups. Examples of aryl are the same as those of the aryl group.

R may have 1 to 8, preferably 1 to 6 substituents. Examples of the substituents include halogen atoms (e.g., fluorine atoms, chlorine atoms, bromine atoms, and iodine atoms), hydroxyl, amino, thiol, cyano, nitro, oxo, imide, carboxyl, amide, sulfonyl, nitro, formyl groups, and hydrocarbon groups having 1 to 6 carbon atoms.

More preferably, the compound represented by the formula (I) may also be a compound represented by a formula (II): $R^1$—X—$R^2$—$CH_2CH(NH_2)COOH$. $R^1$ and $R^2$ each independently represent the aforementioned hydrocarbon group or the aforementioned aryl group, preferably the aforementioned cycloalkyl group or the aforementioned aryl group, and particularly preferably the aforementioned aryl group. —X— represents —O—, —S—, —NH— or a bonding, preferably —O—, —S—, or —NH—, more preferably —O— or —S—, and particularly preferably —O—. $R^1$ may have 1 to 4 and preferably 1 to 3 substituents. $R^2$ may have 1 to 4, preferably 1 to 3 and more preferably 1 to 2 substituents. The substituents for $R^1$ and $R^2$ are the same as those described for R.

Still more preferably, the compound represented by the formula (II) may be a tyrosine derivative biosynthesized from tyrosine as shown below. The tyrosine derivative includes thyroid hormones (e.g., triiodothyronine, thyroxine). The tyrosine derivative may also be a metabolite of the thyroid hormone. Examples of the metabolite of the thyroid hormone include compounds in which a hydroxyl group is added to the thyroid hormone, and the conjugates as described above. The small substance may further be a thyroid hormone-like therapeutic drug or a metabolite thereof.

[Chemical 2]

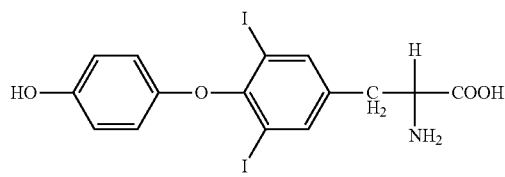

Diiodothyronine (T2)

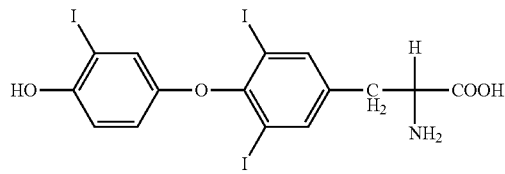

Triiodothyronine (T3)

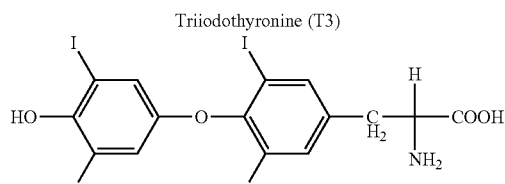

Tetraiodothyronine (T4)

In still another embodiment, the small substance may be vitamin. Examples of vitamin include vitamins A, B1, B2, B6, B12, C, D, E, and K. Preferably vitamin is lipophilic vitamin (e.g., vitamins A, D, E, and K), and more preferably vitamin D as described below. The small substance may also be a metabolite of vitamin. Examples of the metabolite of vitamin include compounds in which a hydroxyl group is added to the aforementioned vitamin, and the aforementioned conjugates. The small substance may further be a vitamin-like therapeutic drug or a metabolite thereof.

[Chemical 3]

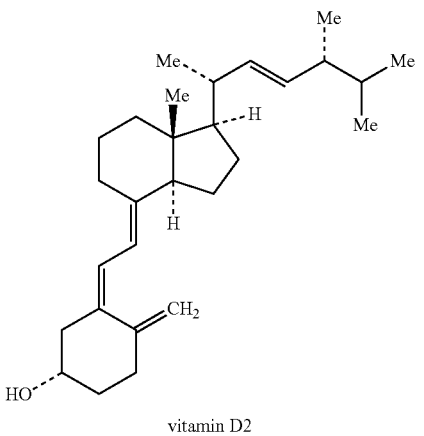

vitamin D2

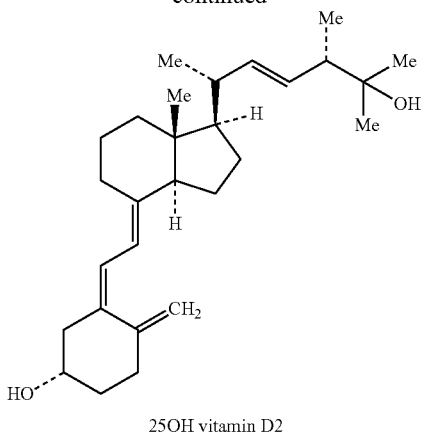

25OH vitamin D2

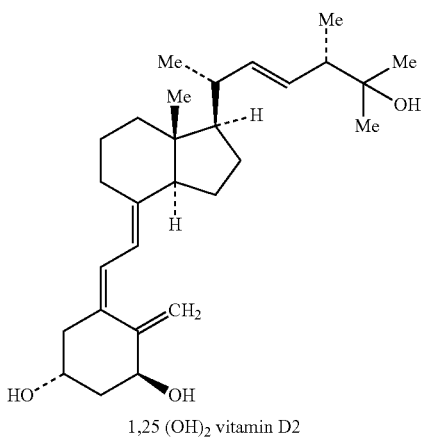

1,25 (OH)₂ vitamin D2

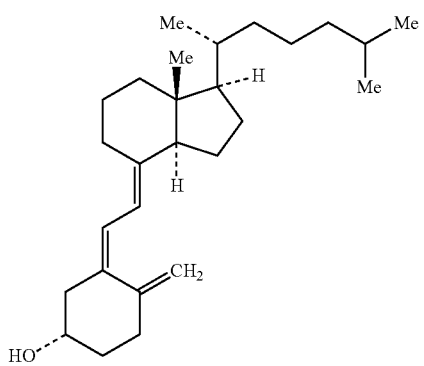

vitamin D3

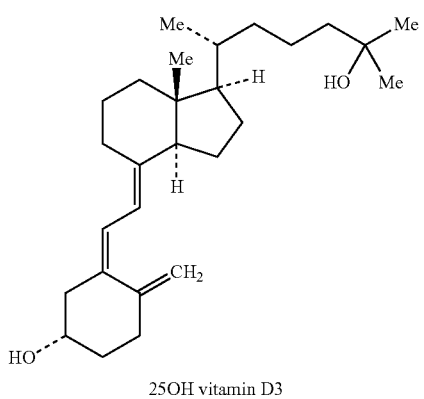

25OH vitamin D3

-continued

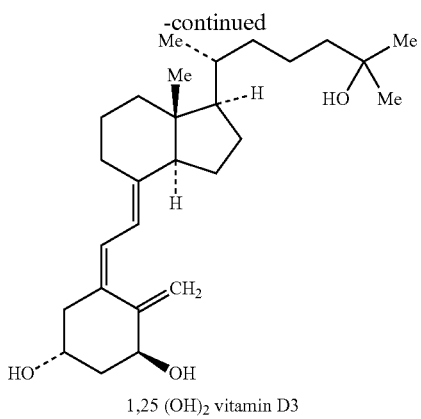

1,25 (OH)$_2$ vitamin D3

The affinity complex is a complex comprising two or more factors as described above. Specifically, the affinity complex include a complex comprising a small substance and a protein (e.g., antibody), a protein complex comprising two or more proteins, a complex comprising a protein and a nucleic acid, a metal requirement protein complex comprising a protein and a metal, a protein aggregate, a nucleic acid complex comprising two or more complementary nucleic acids (e.g., double strands, triple strands), and a metal complex.

In terms of efficiently producing an antibody capable of specifically binding to an affinity complex, the affinity complex preferably has a strong binding affinity between the factors that constitute the affinity complex. Therefore, in terms of efficiently producing the antibody, the affinity complex may be identified by the binding affinity between the factors that constitute the affinity complex. The preferable binding affinity include the affinity having a dissociation constant (i.e., Kd) of less than $10^{-5}$ M, less than $5 \times 10^{-5}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, or less than $10^{-11}$ M. The dissociation constant may also be $10^{-15}$ M or more, $5 \times 10^{-15}$ M or more, $10^{-14}$ M or more, $5 \times 10^{-14}$ M or more, $10^{-13}$ M or more, $5 \times 10^{-13}$ M or more, $10^{-12}$ M or more, $5 \times 10^{-12}$ M or more, $10^{-11}$ M or more, $5 \times 10^{-11}$ M or more, $10^{-10}$ M or more, or $5 \times 10^{-10}$ M or more. Even when the binding affinity between the factors that constitute the affinity complex is low, the formation of the affinity complex can be facilitated by increasing the concentration of the factors in a solution, and thus the antibody can be produced efficiently. Therefore, the binding affinity between the factors that constitute the affinity complex is not necessarily important.

The phrase "capable of specifically binding to an (the) affinity complex" refers to an ability to bind to the affinity complex more preferentially than each factor that constitutes the affinity complex. For example, the antibody of the present invention has the ability to bind to the affinity complex and substantially cannot have an ability to bind to each factor that constitutes the affinity complex. Therefore, the antibody of the present invention may be identified by a cross-reactivity to each factor (e.g., small substance, protein) that constitutes the affinity complex or an analogous factor thereof (e.g., analog of the small substance, homolog protein). For example, when the binding rate of the antibody of the present invention to the objective affinity complex is calculated as 100%, the binding rate of the antibody of the present invention to each factor that constitutes the affinity complex or the analogous factor thereof or an affinity complex comprising the analogous factor (analogous affinity complex) may be 20% or less, 15% or less, 10% or less, 9% or less, 8% or less, 7% or less, 6% or less, 5% or less, 4% or less, 3% or less, 2% or less, 1% or less, or 0.5%, 0.1% or 0.05% or less.

For example, the antibody of the present invention may be those exhibiting the binding rate shown in following (a) to (c):

(a) when a binding rate of an antibody (antibody I) capable of specifically binding to an affinity complex comprising estradiol and an anti-estradiol antibody (affinity complex I) to the affinity complex I is calculated as 100%, a binding rate of the antibody I to an affinity complex comprising estrone and the anti-estradiol antibody (affinity complex I'), an affinity complex comprising estriol and the anti-estradiol antibody (affinity complex I"), an affinity complex comprising an estradiol conjugate and the anti-estradiol antibody (affinity complex I'''), an affinity complex comprising estramustine and the anti-estradiol antibody (affinity complex I''''), or an affinity complex comprising estromustine and the anti-estradiol antibody (affinity complex I''''') is the above value or less;

(b) when a binding rate of an antibody (antibody II) capable of specifically binding to an affinity complex comprising triiodothyronine and an anti-triiodothyronine antibody (affinity complex II) to the affinity complex II is calculated as 100%, a binding rate of the antibody II to an affinity complex comprising diiodothyronine and the anti-triiodothyronine antibody (affinity complex II') or an affinity complex comprising thyroxine and the anti-triiodothyronine antibody (affinity complex II") is the above value or less; or (c) when a binding rate of an antibody (antibody III) capable of specifically binding to an affinity complex comprising 25OH vitamin D3 and an anti-25OH vitamin D3 antibody (affinity complex III-1) or an affinity complex comprising 25OH vitamin D2 and an anti-25OH vitamin D2 antibody (affinity complex III-2) to the affinity complex III-1 or III-2 is calculated as 100%, a binding rate of the antibody III to an affinity complex comprising 1,25(OH)$_2$ vitamin D3 and the anti-25OH vitamin D3 antibody or the anti-25OH vitamin D2 antibody (affinity complex III') or an affinity complex comprising 1,25(OH)$_2$ vitamin D2 and the anti-25OH vitamin D3 antibody or the anti-25OH vitamin D2 antibody (affinity complex III") is the above value or less.

The antibody capable of specifically binding to the affinity complex can also have an ability to bind more preferentially to the affinity complex than a covalent complex (each factor that constitutes the covalent complex is the same as each factor that constitutes the affinity complex). The antibody of the present invention is produced using the affinity complex itself as an antigen, and thus can bind more specifically to the affinity complex than to the covalent complex. Therefore, the antibody of the present invention may be identified by the binding affinity for the affinity complex. The binding affinity of the antibody of the present invention for the affinity complex include the affinity having the dissociation constant (i.e., Kd) of less than $10^{-5}$ M, less than $5 \times 10^{-5}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, or less than $10^{-11}$ M. The dissociation constant of the antibody of the present invention for the affinity complex may also be $10^{-15}$ M or more, $5 \times 10^{-15}$ M or more, $10^{-14}$ M or more, $5 \times 10^{-14}$ M or more, $10^{-13}$ M or more, $5 \times 10^{-13}$ M or more, $10^{-12}$ M or more, $5 \times 10^{-12}$ M or more, $10^{-11}$ M or more, $5 \times 10^{-11}$ M or more, $10^{-10}$ M or more, $5 \times 10^{-10}$ M or more $10^{-9}$ M or more, or $5 \times 10^{-9}$ M or more.

The antibody of the present invention may be a monoclonal antibody. The antibody of the present invention may be of any isotypes such as IgG, IgM, IgA, IgD, IgE, IgY, and the like, but is, for example, IgG or IgM.

The antibody of the present invention may have a region derived from immunoglobulin from the animal having the ability of gene conversion (e.g., variable region, complementarity-determining region, framework region, or constant region). Examples of the region derived from immunoglobulin from the animal having the ability of gene conversion include a variable region (VR) and a constant region (CR) as well as a complementarity-determining region (CDR) and a framework region (FR) found in VR. Examples of VR include a heavy chain variable region (VH) and a light chain variable region (VL). Examples of CR include a heavy chain constant region (CH including CH1, CH2, CH3 and CH4) and a light chain constant region (CL).

The term "gene conversion" refers to that a variable region gene that has undergone V(D)J rearrangement is substituted with a pseudogene present in upstream of the V gene. In birds such as chickens and mammalian animals such as cattle, sheeps and rabbits (animals having the ability of the gene conversion), the variable region of an antibody gene in an antibody-producing cell can be diversified by both the V(D)J rearrangement that is a site-specific recombination and the gene conversion that is one of homologous recombinations. On the other hand, in mammalian animals such as human beings and mice (animal not having the ability of the gene conversion), the variable region of an antibody gene in an antibody-producing cell can be diversified by the V(D)J rearrangement, but cannot be diversified by the gene conversion. In the method of producing the antibody of the present invention as described hereinafter, a population of highly diverse antibody-producing cells (i.e., population of diverse antibody-producing cells having an ability to produce diverse antibodies) is preferably used. Thus, the antibody of the present invention, which is produced by such antibody-producing cells, can have the region derived from immunoglobulin from the animal having the ability of the gene conversion.

Hereinafter, the animal having the ability of the gene conversion is sometimes abbreviated as an animal X. Also, the animal not having the ability of the gene conversion is sometimes abbreviated as an animal Y.

As far as the present inventors have figured out, an antibody against a complex (particularly an affinity complex) appears not to be artificially produced in the animal X. Therefore, the antibody of the present invention having the region derived from immunoglobulin from the animal X is believed to be novel for the conventional antibodies produced in vivo.

The antibody of the present invention may have a first region derived from the immunoglobulin from the animal X (e.g., VR, CR, CDR, FR) and/or a second region derived from the immunoglobulin from the animal Y (e.g., VR, CR, CDR, FR). For example, the antibody of the present invention may have VR comprising CDR, FR or both CDR and FR as the first region derived from the immunoglobulin from the animal X, and CR, FR or both CR and FR as the second region derived from the immunoglobulin from the animal Y. Such an antibody can correspond to an antibody and the like as described hereinafter.

Preferably, the antibody of the present invention may have (I) (a) a heavy chain having a first region (e.g., VR, CDR, FR) derived from the immunoglobulin (e.g., IgM) from the animal X and a second region (e.g., CR, CH1, CH2, CH3) derived from the immunoglobulin (e.g., IgG) from the animal Y and (b) a light chain (e.g., λ chain, κ chain and chimera chains of the λ chain and the κ chain) having a first region (e.g., VR, CDR, FR) derived from the immunoglobulin (e.g., IgM) from the animal X and a second region (e.g., CR) derived from the immunoglobulin (e.g., IgG) from the animal Y, or (II) (a) a heavy chain having a first region (e.g., VR, CDR, FR, CR, CH1) derived from the immunoglobulin (e.g., IgM) from the animal X and a second region (e.g., CR, CH2, CH3) derived from the immunoglobulin (e.g., IgG) from the animal Y and (b) a light chain (e.g., λ chain, κ chain) having VR and CR derived from the immunoglobulin (e.g., IgM) from the animal X.

More preferably, the antibody of the present invention may have (I') (a') a heavy chain having VR derived from chicken IgM and CR(CH1, CH2, CH3) derived from the animal Y (e.g., mouse, human) IgG (e.g., IgG1) and (b') a light chain (e.g., λ chain, κ chain and chimera chains of the λ chain and the κ chain) having VR derived from the chicken IgM and CR derived from the animal Y (e.g., mouse, human) IgG (e.g., IgG1), or (II') (a') a heavy chain having VR and CH1 derived from the chicken IgM and CH2 and CH3 derived from IgG (e.g., IgG1) from the animal Y (e.g., mouse, human) and (b') a light chain (e.g., λ chain, κ chain) having VR and CR derived from the chicken IgM.

Nucleotide sequences of the aforementioned immunoglobulin genes from the animals are known. Thus, those skilled in the art can appropriately produce such genes using gene engineering techniques (see e.g., Examples 5 and 6). The antibodies of (I) and (I') can correspond to chimera type I antibodies described hereinafter. The antibodies of (II) and (II') can correspond to chimera type II antibodies described hereinafter.

The antibody of the present invention may be a full-length antibody. The term "full-length antibody" refers to an antibody comprising heavy and light chains each comprising variable and constant regions (e.g., antibody comprising two Fab portions and an Fc portion). The antibody of the present invention may also be an antibody fragment derived from such a full-length antibody. The antibody fragment is a portion of the full-length antibody, and examples thereof include F(ab')$_2$, Fab', Fab, and Fv.

A traditional antibody produced in vitro is conventionally a so-called single chain antibody (scFv) and can have no constant region. Therefore, the full-length antibody and the antibody fragment of the present invention are believed to be novel for the traditional antibodies produced in vitro. It is known in general terms that a binding force to an antigen and/or the specificity for the antigen is lost or notably reduced when the single chain antibody is modified to the full-length antibody. Therefore, the full-length antibody of the present invention is superior to the traditional single chain antibody produced in vitro and the full-length antibody that can be induced therefrom. The method of the present invention described hereinafter is advantageous in that the full-length antibody can be acquired, a population of diverse antibody-producing cells (library of antibodies) can be prepared in a short period of time (several days), and a true positive clone can be obtained by one screening manipulation (probably because non-specific reactions are inhibited due to a size of the antibody-producing cells (e.g., DT40 cells) used for an assay).

The antibody of the present invention can also be an antibody capable of specifically binding to a portion exposed on the surface of the affinity complex (i.e., neutralization antibody against the complex). According to the method of the present invention as described hereinafter, such an antibody can be produced. For example, when the affinity complex works by forming a heterogeneous multimer (e.g., heterogeneous trimer by three types of proteins) in vivo, occurrence of a biological signal mediated by the formation of the heterogeneous multimer can be prevented by using an antibody capable of specifically binding to a dimer (affinity complex) associated each other among the heterogeneous multimer.

The antibody of the present invention can also be an antibody capable of specifically binding to an immunogenic affinity complex or a non-immunogenic affinity complex (i.e., hapten). Immunogenicity refers to an ability to induce an antibody response in an animal. The method of the present invention as described hereinafter can also produce not only the antibody capable of specifically binding to the immunogenic affinity complex but also the antibody capable of specifically binding to the non-immunogenic affinity complex (i.e., hapten). The method of the present invention acquires an antibody producing-cell that produces the antibody capable of binding to the affinity complex from the population of diverse antibody-producing cells (synonymous with the library of diverse antibodies). Therefore, even when the affinity complex itself is not immunogenic, it is possible to obtain the antibody producing-cell that produces the antibody capable of binding to the affinity complex.

The antibody of the present invention can also be an antibody capable of specifically binding to a complex comprising a factor derived from any animal. Even when a part or all of the factors that constitute the affinity complex are derived from any animal, the method of the present invention described hereinafter can produce an antibody capable of specifically binding to such an affinity complex. In conventional methods using the animal, no immune response to a factor derived from an allogeneic animal can be induced (e.g., when a mouse is immunized with a complex comprising an antigen and a murine antibody thereto). Thus, no antibody against such a factor can be produced. However, the method of the present invention can produce the antibody capable of specifically binding to the complex comprising the factor derived from any animal.

The antibody of the present invention can also be an antibody capable of specifically binding to the affinity complex by specifically recognizing an association portion between the factors in the affinity complex and/or a changed steric structure of the factors caused by the association (e.g., folding and/or conformation).

The antibody of the present invention may be a chimera antibody, a humanized antibody, or a human antibody.

The chimera antibody means a monoclonal antibody having VR and CR derived from immunoglobulins from mutually different animal species. For example, the chimera antibody can be a chimera (animal X/animal Y) antibody having VR derived from the immunoglobulin from the animal X (e.g., chicken) and CR derived from the immunoglobulin from the animal Y (e.g., human). Each CR derived from the immunoglobulin from the animal Y has an inherent amino acid sequence due to an isotype such as IgG, IgM, IgA, IgD, IgE and IgY, and the like. CR of the chimera antibody of the present invention may belong to any isotype.

The chimera antibody can be produced by methods known per se (e.g., see Morrison, Science 229: 1202 (1985); Oi et al., BioTechniques 4:214 (1986); Gillies et al., (1989) J. Immunol. Methods 125: 191-202; U.S. Pat. Nos. 5,807, 715; 4,816,567 and 4,816,397). Specifically, the chimera antibody can be produced as follows. First, a $C_H$ gene (C gene encoding CR of the H chain) obtained from DNA encoding the immunoglobulin from the animal Y is ligated to downstream of a $V_H$ gene (a VDJ gene encoding VR of the H chain) obtained from DNA encoding an animal X monoclonal antibody isolated from an antibody-producing cell derived from the animal X. Subsequently, a $C_L$ gene (C gene encoding CR of the L chain) obtained from DNA encoding the immunoglobulin from the animal Y is ligated to downstream of a $V_L$ gene (a VJ gene encoding VR of the L chain) obtained from DNA encoding the animal X monoclonal antibody isolated from the antibody-producing cell derived from the animal X. Then these ligated products are inserted into one expression vector or separate expression vectors so that they can be expressed respectively. A host cell is transformed with the resulting expression vector(s). The chimera antibody can be obtained by culturing the obtained transformed cell (e.g., see Examples 5 and 6). The present invention also provides a method of producing the chimera antibody comprising converting the antibody of the present invention to the chimera antibody.

The humanized antibody means a monoclonal antibody that is produced by gene engineering and in which, for example, a part or all of CDR is derived from a monoclonal antibody from the animal X (e.g., chicken) and FR and CR are derived from human immunoglobulin. CDR is a region that is present in a hypervariable region (HVR) in VR of an antibody and binds complementarily to an antigen (e.g., CDR1, CDR2, and CDR3). FR is a region that is present before and after CDR and is relatively conserved (e.g., FR1, FR2, FR3, and FR4). In other words, the humanized antibody means a monoclonal antibody in which all regions other than a part or all of CDR in the monoclonal antibody from the animal X (e.g., chicken) are substituted with corresponding regions in the human immunoglobulin.

The humanized antibody can be produced by methods known per se [see e.g., CDR graft (European Patent No. 239,400; WO91/09967; U.S. Pat. Nos. 5,225,539; 5,530,101 and 5,585,089), veneering or resurfacing (European Patents No. 592,106; 519,596; Padlan, Molecular Immunology 28 (4/5): 489-498 (1991); Studnicka et al., Protein Engineering 7(6):805-814 (1994); Roguska et al., PNAS 91:969-973 (1994)), and chain shuffling) (U.S. Pat. No. 5,565,332)]. An amino acid residue(s) in FR may be substituted with a corresponding residue(s) derived from a CDR donor antibody in terms of keeping (preferably improving) antigen binding capacity. The amino acid residue to be substituted in FR can be determined by a well-known method in the art, and can be determined by, for example, modeling of an interaction between CDR and FR for identifying an amino acid residue in FR, which is important for antigen binding, and alignment for identifying an abnormal FR amino acid residue(s) at particular position (see e.g., Queen et al., U.S. Pat. No. 5,585,089; Riechmann et al., Nature 332:323 (1988)). Specifically, the humanized antibody can be produced as follows. First, an H chain CDR gene of the animal X and an L chain CDR gene corresponding thereto of the animal X are isolated from an antibody-producing cell that produces an animal X monoclonal antibody. And, a human H chain gene encoding all regions other than human H chain CDR that corresponds to animal X H chain CDR and a human L chain gene encoding all regions other than human L chain CDR that corresponds to animal X L chain CDR are isolated from a human immunoglobulin gene. Then, CDR is grafted. Subsequently, the human H chain gene in which CDR was grafted and the human L chain gene in which CDR was grafted are inserted into one expression vector or separate expression vectors so that they can be expressed respectively. A host cell is transformed with the resulting expression vector(s). The humanized antibody can be obtained by culturing the resulting transformed cell. The present invention also provides a method of producing a humanized antibody comprising converting the antibody of the present invention to the humanized antibody.

The human antibody means an antibody in which all regions including VR and CR of the H chain and the L chain that constitute immunoglobulin are derived from a gene encoding the human immunoglobulin.

The human antibody can be produced by methods known per se. For example, the human antibody can be produced by using an antigen-producing cell isolated from a transgenic animal produced by incorporating a human immunoglobulin gene or a chromosome including it into a non-human animal (e.g., animal X, non-human animal Y) (by incorporating into a locus in the non-human animal by homologous recombination), or by using a transgenic antibody-producing cell in which the human immunoglobulin gene or the chromosome including it was introduced. A transgenic animal is transgenic for the human immunoglobulin and may be an animal that does not express endogenous immunoglobulin. Animals such as mice and cattle (and/or antibody-producing cells) are known as transgenic animals that produce a human antibody (and/or transgenic antibody-producing cells that produce the human antibody). Production of such a transgenic animal (and/or a cell) and/or production of the human antibody are disclosed in, for example, WO98/37757, WO00/10383, WO00/075300, WO2002/070648, WO2003/047336, WO2003/085107, WO2005/104835, WO2006/047367, JP 2001-231403 A, JP 2009-82033 A, U.S. Pat. No. 5,939,598 and/or Lonberg and Huszar, Int. Rev. Immunol. 13: 65-93 (1995); WO098/24893; WO92/01047; WO96/34096; WO96/33735; WO98/24893; WO92/01047; WO96/34096; WO96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598. The antibody of the present invention (e.g., humanized antibody and human antibody) may be a recycling antibody that is produced to impart pH dependency to an antigen/antibody reaction and can repeatedly block the antigen/antibody reaction (see e.g., Nature Biotechnology, 28, 1203-1207 (2010). The present invention also provides a method of producing the human antibody.

The antibody of the present invention may be modified by determining its nucleotide sequence and using well-known methods in the art (e.g., recombinant DNA technology, site-specific mutagenesis, PCR, and the like (see e.g., technologies described in Sambrook et al., 1990, Molecular Cloning, A Laboratory Manual, 2nd Edition, Cold Spring Harbor Laboratory, Cold Spring Harbor, N.Y. and edited by Ausubel et al., 1998, Current Protocols in Molecular Biology, John Wiley & Sons, NY)). For example, an amino acid residue(s) may be mutated (e.g., substituted, deleted, and/or inserted). The antibody of the present invention may be linked to another moiety or substance, or a solid phase such as a support, as described hereinafter.

The antibody of the present invention can be isolated or purified by known methods concerning proteins such as immunoglobulin. Examples of such a method include chromatography (e.g., ion exchange chromatography, affinity chromatography, and size column chromatography), centrifugation, dialysis, and a method of taking difference in solubility. The antibody of the present invention can also be purified easily by using a substance (e.g., protein) having the affinity for the constant region of the antibody (e.g., constant region of particular isotype), or by fusing to a heterogeneous polypeptide sequence.

(2. Antibody-Producing Cell)

The present invention provides an antibody-producing cell having an ability to produce an antibody capable of specifically binding to an affinity complex. The antibody capable of being produced by the antibody-producing cell and capable of specifically binding to the affinity complex is as described above.

The term "antibody-producing cell" refers to a cell having the ability to produce the antibody. The antibody-producing cell is a cell derived from an animal having the ability to produce the antibody, and includes a B cell. The antibody-producing cell can be a cell derived from an animal such as a mammalian animal (e.g., human, mouse, rat, cattle, sheep) and a bird (e.g., chicken). The antibody-producing cell include a primary cultured cell and a cell line, and the cell line is preferred.

The antibody-producing cell can be preferably an antibody-producing cell capable of causing further mutation(s) in the variable region in addition to the V(D)J rearrangement. One example of the antibody-producing cell capable of causing the further mutation(s) in the variable region is an antibody-producing cell that is derived from the animal having the ability of the gene conversion and keeps such an ability. Another example of the antibody-producing cell capable of causing the further mutation(s) in the variable region is an antibody-producing cell capable of causing somatic mutation in the variable region. As the antibody-producing cell capable of causing the somatic mutation in the variable region, the antibody-producing cell capable of remarkably enhancing a frequency of the somatic mutation in the variable region has been reported, and for example, cells derived from lymphoma (e.g., Burkitt's lymphoma, follicular lymphoma, diffuse large cell lymphoma) can be used. The production of such an antibody-producing cell has been disclosed in, for example, prior references such as Buerstedde et al., [EMBO J. (1990) 9: 921-927], WO2004/011644, WO2004/058964, WO2002/100998, and the like.

The antibody-producing cell may be preferably derived from the animal having the ability of the gene conversion. The antibody-producing cell derived from the animal having the ability of the gene conversion may be a knockout cell. Such a knockout cell includes XRCC (e.g., one or more XRCC molecular species such as XRCC1, XRCC2, and XRCC3) knockout cells. More preferably, the antibody-producing cell is a bursa of Fabricius lymphoma cell such as DT40 cell. DT40 cell is a chicken-derived B cell line, and also includes a derivative line and a subline in which a mutation (e.g., recombination, insertion, deletion, and the like of a certain gene) was introduced into a chromosome possessed by this cell (see e.g., WO2004/011644).

The antibody-producing cell may also be a cell in which homologous recombination at an antibody gene locus has occurred to produce the immunoglobulin having a certain isotype. Examples of the certain isotype include IgG, IgM, IgA, IgD, IgE, and IgY.

The antibody-producing cell may also be a transformant produced by introducing an expression vector of the antibody of the present invention or the other protein into a host cell. The expression of an exogenous gene via the expression vector can be transient or constitutive (i.e., stable). Examples of the host cell include microorganisms such as bacteria (e.g., *Escherichia coli*) and yeast, and animal cells such as insect cell, bird cell and mammalian cell (e.g., CHO cell, MDCK cell). The present invention also provides such an expression vector used for producing the transformant.

A promoter used in the expression vector is not particularly limited as long as the promoter can work in a cell to which the promoter is introduced, and examples thereof include promoters that can work in the microorganisms and the animal cells. Examples of such a promoter include viral promoters (e.g., SV40 derived early promoter, cytomegalovirus LTR, Rous sarcoma virus LTR, MoMuLV derived LTR, adenovirus derived early promoter), and constitutive gene promoters derived from the mammalian animals (e.g., β-actin gene promoter, PGK gene promoter, and transferrin gene promoter).

The expression vector preferably comprises a transcription termination signal (i.e., terminator region) at downstream of an oligo (poly) nucleotide encoding a nucleic acid molecule. Further, the expression vector may comprise a gene resistant to a drug (e.g., ampicillin, kanamycin, G418).

A basic vector for the expression vector used for introducing the exogenous gene into a tumor cell can be, for example, a plasmid or a viral vector (e.g., vector derived from adenovirus, retrovirus, adeno-associated virus, herpes virus, vaccinia virus, pox virus, poliovirus, sindbis virus, Sendai virus, lentivirus, or the like).

(3. Method of Producing Antibody-producing Cell)

The present invention provides a method of producing an antibody-producing cell having an ability to produce an antibody capable of specifically binding to an affinity complex. The present method comprises preparing the antibody-producing cell having the ability to produce the antibody capable of specifically binding to the affinity complex from a population of diverse antibody-producing cells using the affinity complex. The affinity complex, the antibody capable of specifically binding to the affinity complex, and the antibody-producing cell are as described above. For example, such a preparation is carried out by seeding diverse antigen-producing cells in different wells and culturing them followed by evaluating whether the antibody capable of specifically binding to the affinity complex is present or not in a culture supernatant. Alternatively, such a preparation is carried out by selecting the antibody-producing cell having the ability to bind to the affinity complex from the population of the diverse antigen-producing cells. Such a preparation can be carried out in a solution such as medium, buffer, or water. That is, such a preparation can be carried out in vitro.

In the present invention, any suitable medium is used depending on an objective step. For example, concerning a given cell, examples of basic medium used for preparing the medium include MEM, IMDM, DMEM, α-MEM, Ham Medium, RPMI medium, Fisher's medium, and mixed medium thereof. The medium can contain, for example, serum (e.g., chicken serum, bovine serum such as FCS), serum alternative (e.g., KSR), a fatty acid or lipid, an amino acid, vitamin, a growth factor, a cytokine, an anti-oxidant, 2-mercaptoethanol, a pyruvic acid, buffer, an inorganic salt, and the like. Other culture conditions such as culture temperature and $CO_2$ concentration can be determined appropriately. The culture temperature is not particularly limited, and is, for example, about 30 to 40° C., preferably about 39.5° C. The $CO_2$ concentration is, for example, about 1 to 10%, preferably about 5%. The other conditions such as a cell number in the cultivation and the concentration of various factors can be determined appropriately. Examples of given cells that can be used in the present invention include cells (e.g., CHO cells, MDCK cells) derived from mammalian animals (e.g., human, dog, mouse, rat, rabbit, hamster), cells (e.g., DT40 cells) derived from birds (e.g., chicken), and cells derived from insects.

In the present invention, any suitable buffer is used depending on an objective step. Examples of such buffer include phosphate buffer (e.g., PBS, PBST), Tris buffer (e.g., Tris/HCl), carbonate buffer, acetate buffer, citrate buffer, borate buffer, and tartrate buffer. The buffer may further contain substances such as salts. A pH value of the buffer is adjusted appropriately depending on the objective step, and is, for example, pH 4.0 to 10.0, preferably pH 5.0 to 9.0, more preferably pH 6.0 to 8.0, and still more preferably pH 6.5 to 7.5.

Preferably, the preparation of the antibody-producing cell having the ability to produce the antibody capable of specifically binding to the affinity complex from the population of the diverse antibody-producing cells is carried out by selecting the antibody-producing cell having the ability to bind to the affinity complex from the population of the diverse antibody-producing cells using the affinity complex. The antibody-producing cell having the ability to produce the antibody capable of specifically binding to the affinity complex may be produced by using an affinity complex that keeps an ability to associate and comprises a portion of a natural factor (e.g., ligand binding domain, extracellular domain, soluble receptor). The affinity complex may be labeled with a substance for detection as described hereinafter. The affinity complex may be fixed to a solid directly or indirectly through a linker (e.g., protein G). The solid may be labeled with the substance for detection as described hereinafter. Examples of the solid to which the affinity complex may be fixed include particles (e.g., magnetic particles, fluorescence labeled particles). Specifically, the preparation may be carried out as follows. First, a population of diverse antibody-producing cells and a solid to which an affinity complex was fixed are mixed in a solution (e.g., buffer), and reacted at predetermined temperature (e.g., 0 to 40° C., preferably 2 to 10° C.) for a predetermined period of time (e.g., 5 to 300 minutes, preferably 15 to 60 minutes). A density of the antibody-producing cells in the solution may be, for example, $1.0 \times 10^5$ to $1.0 \times 10^{10}$ cells/ml, $1.0 \times 10^6$ to $1.0 \times 10^9$ cells/ml, or $1.0 \times 10^7$ to $5.0 \times 10^8$ cells/ml. In order to prevent from acquiring the antibody-producing cells having the ability to produce not the antibody capable of specifically binding to the affinity complex but the antibody capable of binding to each factor that constitutes the affinity complex (i.e., blocking), the solution for the reaction may comprise at least one or a plurality of factors that constitutes the affinity complex in addition to the affinity complex. Then, the antibody-producing cells bound to the affinity complex fixed to the solid are collected from the population of the diverse antibody-producing cells by any technique (e.g., magnetic or fluorescent method). If necessary, the collected antibody-producing cells are suspended in medium to separate the antibody-producing cells from the solid to which the affinity complex was fixed. Subsequently, the antibody-producing cells are cultured. The obtained antibody-producing cells can produce the antibody capable of specifically binding to the affinity complex.

It may be confirmed whether the obtained antibody-producing cells produce the antibody capable of specifically binding to the affinity complex or not. Such a confirmation can be carried out, for example, using the affinity complex. Specifically, the confirmation may be carried out as follows. First, at least one factor that constitutes the affinity complex is fixed on a support (e.g., plate). Then, a culture supernatant of the antibody-producing cells is added thereto in the presence or absence of the other factor(s) that constitutes the affinity complex. Finally, using a detection means for the antibody capable of specifically binding to the affinity complex [e.g., an enzyme (e.g., HRP) bound to an anti-immunoglobulin (e.g., IgM) antibody capable of binding to a constant region of the antibody, and its substrate (e.g., TMB)], it is evaluated whether the antibody capable of specifically binding to the affinity complex is contained or not in the culture supernatant of the antibody-producing cells.

The specificity of the antibody produced by the antibody-producing cell for a heterogeneous complex can be confirmed by the methodology described above. On the other hand, the specificity of the antibody produced by the antibody-producing cell for a homogeneous complex cannot be confirmed by the methodology described above. Because homogeneous factors (monomers) that constitutes the homogeneous complex are autonomously associated to form the complex in the solution, and cannot be present as the monomers. Therefore, further evaluation is required in regard to that the antibody produced by the antibody-producing cell is specific for the homogeneous complex and cannot bind to the monomer capable of forming the homogeneous complex. Such an evaluation can be carried out by, for example, (i) producing a mutant factor in which an amino acid mutation (e.g., substitution, deletion, insertion) is introduced into an association portion between factors so that the association becomes impossible and confirming that the antibody of the present invention does not bind to the mutant factor; (ii) producing a fusion factor in which a protein (e.g., GFP, GST) is added to the factor so that the association between the factors is inhibited and confirming that the antibody of the present invention does not bind to the fusion factor; or (iii) confirming using a solution prepared so that the factors do not form the affinity complex. The solution described in (iii) can be prepared by, for example, controlling a condition such as a salt concentration and pH, or adding a heterogeneous factor (b) capable of exhibiting a higher binding strength to a homogeneous factor (a) than a binding strength between the homogeneous factors (a) to the solution, or excessively adding the heterogeneous factor (b) capable of associating with the factor (a) to the solution.

The method of the present invention may further comprise preparing an affinity complex by associating two or more factors mutually having the affinity. The association can be carried out in the solution (e.g., buffer). The factors that constitute the affinity complex are as described above. At least one of two or more factors may previously be fixed to a solid. In this case, the affinity complex to be prepared may be fixed to the solid. The factor may be fixed to the solid, for example, through a linker. For example, when the factor is immunoglobulin, the factor may be fixed to the solid through a protein (e.g., protein G) having the affinity for the immunoglobulin. When two or more factors mutually having the affinity are associated, the concentration of each factor in the solution is not particularly limited as long as the affinity complex is formed, and may be, for example, 0.001 to 100,000 μM, 0.01 to 10,000 μM, 0.05 to 1,000 μM or 0.1 to 100 μM. The affinity complex used in the method of the present invention may be a library comprising various types of the affinity complexes or may be used in an array mode.

The method of the present invention may further comprise providing a population of diverse antibody-producing cells. The population of the diverse antibody-producing cells may be prepared previously or prepared freshly. The population of the diverse antibody-producing cells can be preferably a population of antibody-producing cells capable of causing the further mutation in the variable region in addition of the V(D)J rearrangement. Examples of the population of the diverse antibody-producing cells include the population of antibody-producing cells derived from the animal having the ability of the gene conversion and keeping such an ability, and the population of antibody-producing cells capable of causing the somatic mutation in the variable region, as described above. These populations can be prepared, for example, by the methods described in the reference listed above.

The method of the present invention may further comprise preparing a population of diverse antibody-producing cells by treating the antibody-producing cells having the ability of the gene conversion with an inhibitor of histone deacetylase in the medium. Looseness of a chromatin structure in chromosomes in the antibody-producing cell is first facilitated by such a treatment. Then, the homologous recombination at the antibody locus is facilitated by this looseness of the chromatin structure to yield the population of diverse antibody-producing cells that produce diverse antibodies. Examples of the histone deacetylase inhibitor include protein factors such as antibodies having an activity that inhibits an activity of histone deacetylase (HDAC), and compounds such as trichostatin A, butyric acid and valproic acid. For details of the methods of preparing the population of the diverse antibody-producing cells from the antibody-producing cells having the ability of the gene conversion, see, e.g. WO2004/011644. One example of such technology is known as ADLib (autonomously diversifying library) system.

The method of the present invention may further comprise removing antibody-producing cells having the ability to produce the antibody capable of specifically binding to the factor that constitutes the affinity complex from the population of diverse antibody-producing cells using the factor that constitutes the affinity complex, before preparing antibody-producing cells having the ability to produce the antibody capable of specifically binding to the affinity complex from the population of diverse antibody-producing cells using the affinity complex. The antibody-producing cells having the ability to produce the antibody capable of specifically binding to the affinity complex can be obtained efficiently by such a methodology. For example, when an objective antibody-producing cell is an antibody-producing cell having the ability to bind to the affinity complex, the removal may be performed as follows. First, the factor that constitutes the affinity complex is fixed to the support (e.g., plate) in the solution. Then, a population of diverse antibody-producing cells is added to the solution and is left stand for a predetermined period of time to bind antibody-producing cells having the ability to bind to the factor that constitutes the affinity complex to the factor on the support. A solution containing a population of antibody-producing cells that were not bound to the support is collected. Subsequently, the antibody-producing cells having the ability to produce the antibody capable of specifically binding to the affinity complex are prepared from the population of the diverse antibody-producing cells using the affinity complex. One type of the factors that constitute the affinity complex may be removed, or two or more types (e.g., all) of the factors that constitute the affinity complex may be removed by repeating the removal multiple times.

As described above, there is the possibility that the antibody of the present invention recognizes specifically the association portion between the factors and/or the changed steric structure (e.g., folding and/or conformation) of the factor caused by the association, in the affinity complex.

Therefore, the method of the present invention may further comprise classifying the antibody of the present invention into an antibody capable of specifically binding to the association portion between the factors in the affinity complex, or an antibody capable of specifically binding to the changed steric structure (e.g., folding and/or conformation) of the factor caused by the association, or an antibody having both of the properties described above.

The method of the present invention may be carried out by repeating all or a part of the above steps. For example, an antigen-producing cell that produces a high quality antibody against the affinity complex can be prepared by repeating the above steps two times or more. The method of the present invention may also be carried out by the combination of different methodologies. For example, an antibody-producing cell that produces an optimized antibody against the affinity complex can be prepared by combining the methodology included in ADLib system with somatic cell mutagenesis described above. Of course, the method of the present invention itself is excellent, and thus, is not necessarily combined with the other methodology. The method of the present invention can be used alone in terms of obtaining the objective antibody more rapidly.

(4. Method of Producing Antibody)

The present invention provides a method of producing an antibody capable of specifically binding to an affinity complex. In the present method, the antibody capable of specifically binding to the affinity complex is obtained by culturing an antibody-producing cell having the ability to produce the antibody capable of specifically binding to the affinity complex. The affinity complex, the antibody capable of specifically binding to the affinity complex, and the antibody-producing cell are as described above.

The antibody-producing cell can be cultured in the medium. For example, the aforementioned medium can be used for the animal cells. For the microorganisms, the medium preferably contains a carbon source, a nitrogen source, an inorganics and the like required for growth of microorganisms. Here, examples of the carbon source include glucose, dextrin, soluble starch, sucrose, and the like, examples of the nitrogen source include inorganic or organic substances such as ammonium salts, nitrate salts, corn steep liquor, penton, casein, meat extracts, soybean cake, and potato extract solution, and examples of the inorganics include calcium chloride, sodium dihydrogen phosphate, magnesium chloride, and the like. Yeast extracts, vitamins, and the like may also be added to the medium. The culture conditions such as the temperature, pH of the medium, and the culture period are appropriately selected so that the antibody in a large amount is produced from the antibody-producing cells. The culture temperature is, for example, 30 to 40° C.

The method of producing the antibody may further comprise obtaining the antibody-producing cell having the ability to produce the antibody capable of specifically binding to the affinity complex from the population of the diverse antibody-producing cells in the medium. Such a step can be carried out in the same manner as in the method of producing the antibody-producing cell of the present invention.

(5. Intended Use of Antibody)

The antibody of the present invention is useful, for example, as a reagent (e.g., a diagnostic reagent, an experimental reagent) and a pharmaceutical, and for screening of a factor.

For example, the antibody of the present invention can be used as a reagent for an immunoassay (qualitative or quantitative measurement) of the affinity complex. The immunoassay includes enzyme immunoassay (EIA) (e.g., direct competitive ELISA, indirect competitive ELISA, sandwich ELISA), radioactive immunoassay (RIA), fluorescence immunoassay (FIA), immuno-chromatography, luminescence immunoassay, spin immunoassay, western blotting, and immunohistochemical staining.

When used as the reagent, the antibody of the present invention may be linked to a substance for detection. The antibody of the present invention can be linked to the substance for detection directly or indirectly (i.e., by the use of the linker). Examples of the substance for detection include enzymes (e.g., horseradish peroxidase, alkaline phosphatase), affinity substances (e.g., streptavidin, biotin), fluorescent substances (e.g., fluorescein, fluorescein isothiocyanate, rhodamine), luminescent substances (e.g., luciferin, aequorin), and radioactive substances (e.g., $^{125}$I, $^{131}$I, $^{111}$In, $^{99}$Tc). The antibody of the present invention linked to the substance for detection is useful for the immunoassay.

When used as the reagent, the antibody of the present invention may be fixed onto a support. Examples of the support include membranes (e.g., nitrocellulose membranes), glasses, plastics, metals, and plates (e.g., multi-well plates). The antibody of the present invention fixed onto the support is useful for, for example, the immunoassay and purification of the affinity complex.

The antibody of the present invention is preferably used for a non-competitive assay. Examples of the non-competitive assay include a sandwich method. Preferably when the antibody of the present invention is used for the sandwich method, a first antibody against a factor (e.g., small substance, protein) and a second antibody capable of specifically binding to an affinity complex comprising the factor and the first antibody thereto (i.e., combination of antibodies) are also preferably used.

The antibody of the present invention can cause a loss of a function of the affinity complex or can alter pharmacodynamics of the affinity complex by binding to the affinity complex present in vivo as a pharmaceutical. For example, the antibody of the present invention can be used for inhibiting the formation of the affinity complex composed of at least three factors present in vivo. Specifically, when an affinity complex present in vivo is composed of a factor (a) (e.g., a ligand), a factor (b) (e.g., a receptor), and a factor (c) (e.g., a cofactor such as a coactivator and a corepressor), the antibody of the present invention can inhibit a linkage between the factor (c) and an affinity complex composed of the factor (a) and factor (b) by competitively binding to the affinity complex composed of the factor (a) and factor (b), thereby being capable of regulating a biological signal (e.g., a growth signal) mediated by the formation of the affinity complex composed of the factor (a), the factor (b) and the factor (c). For example, when the factor (c) is the coactivator, the antibody of the present invention can reduce the biological signal. On the other hand, when the factor (c) is the corepressor, the antibody of the present invention can augment the biological signal. Alternatively, when a mutation to augment the biological signal (e.g., the growth signal) occurs in the factor that constitutes the affinity complex present in vivo, the antibody of the present invention can reduce the biological signal by inhibiting the formation of the affinity complex.

When used as the pharmaceutical, the antibody of the present invention may be linked to a substance useful for the treatment. The antibody of the present invention can be linked to the substance useful for the treatment directly or indirectly (i.e., by the use of the linker). Examples of the substance useful for the treatment include anticancer agents, toxins (e.g., inhibiting cell proliferation or killing cells), proteins (e.g., growth factors, cytokines), radioactive metals (e.g., α-emitter (e.g., $^{213}$Bi)), apoptosis accelerators, and stabilizing agents (e.g., PEG). Technology to link such a substance to the antibody is well-known, and see e.g., Amon et al., "Monoclonal Antibodies For Immunotargeting Of Drugs In Cancer Therapy" Monoclonal Antibodies And Cancer Therapy, Reisfeld et al., (edited) 243-56 (Alan R. Liss, Inc. 1985); Hellstrom et al., "Antibodies For Drug Delivery" Controlled Drug Delivery (2nd edition), Robinso et al., (edited) 623-53 (Marcel Dekker, Inc. 1987); Thorpe, "Antibody Carriers Of Cytotoxic Agents In Cancer Therapy: A Review" Monoclonal Antibodies' 84: Biological And Clinical Applications, Pinchera et al., (edited) 475-506 (1985).

When used as the pharmaceutical, the antibody of the present invention is administered as a pharmaceutical composition comprising a pharmaceutically acceptable carrier. The pharmaceutical composition is administered orally or parenterally (e.g., intravenous injection, subcutaneous injection, intramuscular injection, topical injection, intraperitoneal administration). Examples of the pharmaceutically acceptable carrier include, but are not limited to, excipients such as sucrose, starch, mannit, sorbit, lactose, glucose, cellulose, talc, calcium phosphate and calcium carbonate; binders such as cellulose, methylcellulose, hydroxypropylcellulose, polypropyl pyrrolidone, gelatin, gum arabic, polyethylene glycol, sucrose and starch; disintegrants such as starch, carboxymethylcellulose, hydroxypropylstarch, sodium/glycol/starch, sodium hydrogen carbonate, calcium phosphate and calcium citrate; lubricants such as magnesium stearate, Aerosil, talc and sodium lauryl sulfate; flavoring agents such as citric acid, menthol, glycyrrhizin ammonium salts, glycine and orange powders; preservatives such as sodium benzoate, sodium hydrogen sulfite, methylparaben and propylparaben; stabilizers such as citric acid, sodium citrate and acetic acid; suspending agents such as methylcellulose, polyvinyl pyrrolidone and aluminium stearate; dispersants such as surfactants; diluents such as water, saline and orange juice; and base waxes such as cacao butter, polyethylene glycol and paraffin.

When the antibody of the present invention is used as the pharmaceutical, a dosage of the antibody of the present invention varies depending on an activity and a type of an active ingredient, severity of a disease, animal species to be administered, tolerance, a body weight and an age of a subject to be administered, and cannot be determined in general, but is typically about 0.001 to about 500 mg/kg as an amount of the active ingredient per day per adult.

The antibody of the present invention may be used in combination with at least one factor that constitutes the affinity complex. In this case, the antibody of the present invention is provided as a set comprising (i) an antibody capable of specifically binding to the affinity complex and (ii) at least one factor that constitutes the affinity complex. At least one factor that constitutes the affinity complex is the same as the aforementioned factor that constitutes the affinity complex. The set of the present invention may also comprise (i') an antibody capable of specifically binding to an affinity complex comprising a factor (e.g., small substance or protein) and an antibody thereto and (ii') an antibody capable of specifically binding to the factor (e.g., small substance or protein). The set of the present invention may be provided as a kit.

For example, the set of the present invention is useful for detection and/or quantification of the factor capable of constituting the affinity complex. When the antibody of the present invention is provided as such a set, the antibody of the present invention may be linked to the substance for detection as described above. Alternatively, when the antibody of the present invention is not linked to the substance for detection, the set of the present invention may further comprise the substance for detection and/or a protein (e.g., anti-immunoglobulin antibody or protein G) for detecting the antibody of the present invention, which is linked to the substance for detection. For example, when at least one factor that constitutes the affinity complex is the protein, the set of the present invention is useful for the sandwich method.

Alternatively, when at least one factor that constitutes the affinity complex is a protein such as an antibody, the set of the present invention is used for a sandwich therapy (e.g., dual antibody therapy) therapeutically targeting another factor (e.g., small substance or protein) that constitutes the affinity complex.

For example, an antibody does not necessarily have the high specificity for the small substance. However, dual specificity is accomplished and the specificity is amplified by combining an antibody capable of specifically binding to the small substance with an antibody capable of specifically binding to an affinity complex comprising the small substance and an antibody capable of specifically binding thereto. The combination of such antibodies is more specific for the small substance than the single antibody alone. Therefore, the set of the present invention is useful for an antibody therapy to the small substance.

Also an antibody does not necessarily have the high specificity for a certain target protein among a plurality of proteins having high homology. For example, when a therapeutic target is a natural protein (a) and a natural protein (b) (homolog) having the high homology (e.g., 80% or more, 85% or more, 90% or more, 95% or more, 96% or more, 97% or more, 98% or more or 99% or more amino acid identity) to the natural protein (a) is present, the combination of such antibodies can be used in order to allow the antibodies to act more selectively for the natural protein (a). Therefore, the set of the present invention is useful for the antibody therapy therapeutically targeting the certain protein among a plurality of proteins having the high homology.

Further, an antibody does not necessarily have the high specificity for a mutant protein. Examples of such a mutant protein include proteins having one or several amino acid mutations (e.g., substitution, deletion, insertion and/or addition) in natural proteins. For example, in cancer, when it is not desired to therapeutically target a non-mutated protein (a) (natural protein (a)) expressed on normal cells and it is desired to therapeutically target only a mutated protein (a') expressed on abnormal cells, the combination of such antibodies can be used in order to allow the antibodies to more selectively act on the mutated protein (a'). Therefore, the set of the present invention is useful for the antibody therapy therapeutically targeting only the mutated protein.

The set of the present invention is useful for screening of a factor capable of forming an affinity complex. The set of the present invention is also useful for screening of a ligand (e.g., small substance, protein) having a different action mechanism. Those having the different action mechanism (e.g., agonist, antagonist, reverse agonist) are known as the ligands for a given receptor. Such a difference in action mechanism of the ligand for the given receptor can be attributed to the change of the steric structure of receptor (e.g., folding and/or conformation) that can be caused by the association of the receptor and the ligand. Therefore, when the antibody of the present invention capable of specifically recognizing the changed steric structure of the factor caused by the association is used, the antibody potentially serves to identify the type of the action mechanism of the ligand.

The present invention will be described in more detail with reference to following Examples, but the present invention is not limited thereto.

EXAMPLES

Example 1

Acquisition of Antibody Against Affinity Complex (E2/Anti-E2 Antibody Complex)

An antibody against an E2/anti-E2 antibody complex was acquired by performing the following method utilizing in vitro chicken IgM acquisition technology [ADLib (Autonomously Diversifying Library) system: see e.g., WO2004/011644]. Hereinafter, estrone, estradiol and estriol are sometimes abbreviated as E1, E2 and E3, respectively. Also hereinafter, 1 µg/mL of E2 corresponds to 3.7 µM, 1 µg/mL of an F18-3 antibody corresponds to 6.7 nM, 1 µg/mL of an F12-33 antibody corresponds to 6.7 nM, and 1 µg/mL of trichostatin A (TSA) corresponds to 3.3 µM.

(1) Diversification of DT40 Cells

Diversified DT40 cells were produced by the following procedure.

50 mL of IMDM medium containing 9% FBS and 1% chicken serum [CS (Chicken Serum)$^+$ medium] was weighed and added to a 15 cm dish.

Trichostatin A (TSA) was added thereto at a final concentration of 2.5 ng/mL.

DT40 cells at $1.5 \times 10^7$ cells were added thereto and cultured in a $CO_2$ incubator set at 39.5° C. for one day.

(2) Passage of DT40 Cells

DT40 cells were subcultured by the following procedure.

The cell suspension cultured for one day was transferred to a 50 mL tube, and centrifuged at 4° C. at 1,000 rpm for 10 minutes.

After removing a supernatant, the cells were resuspended in 10 mL of the CS$^+$ medium.

The cell suspension was diluted 20 times by adding 50 µL of the cell suspension to 950 µL of the CS$^+$ medium, and stirred.

The number of the living cells was counted.

50 mL of the CS$^+$ medium was added to a new 15 cm dish.

DT40 cells at $1.5 \times 10^7$ cells were added thereto and cultured in the $CO_2$ incubator set at 39.5° C. for one day.

Before selecting cells that produced an objective antibody, the cells were treated twice with TSA. The treatment with TSA was performed by culturing the cells in the CS$^+$ medium containing 2.5 ng/mL of TSA at 39.5° C. overnight.

(3) Preparation of Antigen-Binding Particles

Antigen-binding particles were prepared by the following procedure.

300 µg/mL of the anti-E2 antibody (F18-3) was added to phosphate buffered saline (PBS) (13.5 mg/mL) containing magnetic beads to which protein G had been fixed [Dynabeads Protein G (particle diameter: 2.8 µm) available from Invitrogen, Catalog number: 100.03D]. The anti-E2 antibody (F18-3) is a murine monoclonal antibody established in our company. Binding of the anti-E2 antibody (F18-3) to E2 is estimated to be about $10^{-9}$ M to $10^{-12}$ M from various data.

The mixture was reacted at 4° C. for one hour to immobilize F18-3 onto the particles.

The particles were washed four times with 0.1% BSA/PBS.

The particles were dispersed in PBS containing 1.1 µg/mL of E2.

The mixture was left stand at 4° C. for one hour to form an antigen/antibody complex where the antigen and antibody were associated (affinity complex comprising E2 and the anti-E2 antibody).

The particles were washed four times with 0.1% BSA/PBS.

(4) Culture of Cells Producing Objective Antibody

The cells producing the objective antibody were cultured by the following procedure.

50 mL of the CS$^+$ medium was added to each of two 15 cm dishes.

$1.5 \times 10^7$ cells were added to the each medium and cultured for one day.

The cell suspension was transferred to a 50 mL tube, and centrifuged at 4° C. at 1,000 rpm for 10 minutes.

After removing a supernatant, the cells were washed twice with 1% BSA/PBS, and transferred to a 1.5 mL tube.

The tube was centrifuged at 4° C. at 3,500 rpm for 5 minutes, and a supernatant was removed.

The antigen binding particles prepared in (3) were washed four times with 1% BSA/PBS.

The cells ($9 \times 10^7$ cells/mL) and the antigen binding particles (75 µg/mL) were mixed and reacted at 4° C. for 30 minutes.

The mixture of the cells and the particles was washed five times with 1% BSA/PBS, and excess cells were removed.

The cells/particles were dispersed in CS$^-$ medium.

The cells/particles were seeded in a 96-well plate, and cultured for a week.

(5) Selection of Cells Producing Objective Antibody

The selection was carried out using an antigen/antibody complex-immobilized ELISA. It was evaluated by difference in color development in the presence or absence of E2 whether the cells produced the objective antibody or not. A procedure was as follows.

1 µg/mL of the anti-E2 antibody was added to an assay plate and immobilized by incubating the plate at 37° C. for one hour.

The plate was washed three times with phosphate buffered saline containing 0.05% Tween 20 (0.05% PBST).

The plate was blocked with 1% skim milk/PBS.

The plate was washed three times with PBST.

25 µL of E2 (200 ng/mL) or the buffer alone was added.

25 µL of the culture supernatant was added to perform a primary reaction.

The plate was washed three times with PBST.

An anti-chicken IgM/HRP was added to perform a secondary reaction.

The plate was washed three times with PBST.

TMB (3,3',5,5'-tetramethylbenzidine) was added to perform a color development reaction.

1N sulfuric acid was added to stop the color development reaction.

The color was measured at OD450.

(6) Results

Figure 2:
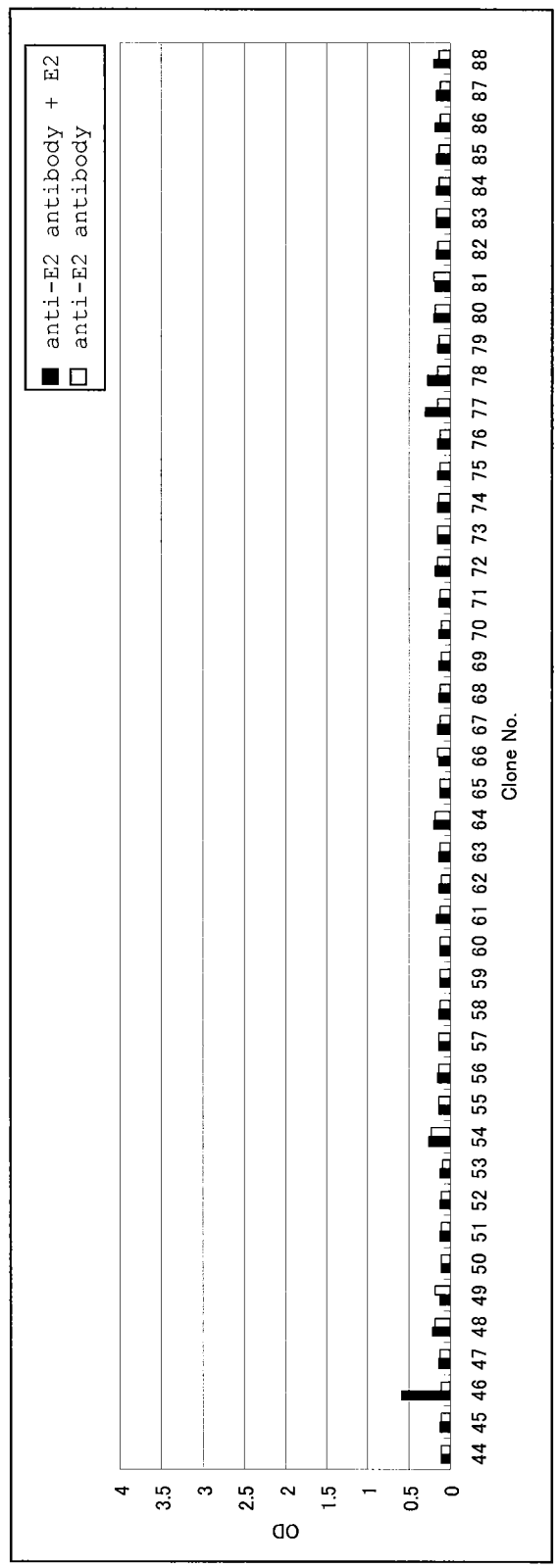
FIG. 2 is a view showing cell clones (No. 44 to 88) obtained by the method of the present invention. One type of cell clone produced an antibody capable of specifically binding to the antigen/antibody complex (affinity complex comprising estrogen and the anti-estrogen antibody)

The cell clones producing the antibody to be bound to the antigen/antibody complex (affinity complex comprising E2 and the anti-E2 antibody) were successfully obtained at high rate in the presence or absence of E2 (100 ng/mL) (3/88=3.4%, see FIGS. 1 and 2). Such an efficiency of producing the antibody cannot be accomplished by the conventional methods of producing the antibody. For example, the efficiency of producing the antibody by the conventional animal immunization method (hybridoma method) never comes close to the above efficiency. The antibody against the affinity complex itself cannot be obtained in the conventional animal immunization method. Therefore, it was demonstrated that the method of the present invention could efficiently produce the antibody against the affinity complex itself.

Example 2

Evaluation of Specificity of Anti-E2 Antibody and Objective Antibody Against E2/Anti-E2 Antibody Complex (1) Method The specificity was evaluated by performing ELISA using the following procedure.

Two types of the anti-E2 antibodies (F18-3 and F12-33) and an anti-AFP antibody (negative control) were added each at 2 μg/mL to an assay plate, and immobilized by incubating the plate at 37° C. for one hour. The anti-E2 antibodies (F18-3 and F12-33) are murine monoclonal antibodies established in our company.

The plate was washed three times with PBST.

The plate was blocked with 1% skim milk/PBS.

The plate was washed three times with PBST.

25 μL of E1 (2 ng/mL), E2 (2 ng/mL) or the buffer alone was added.

25 μL of a culture supernatant of the clones (2-1, 2-2, 2-3, 2-4, 2-5 and 2-6) established by the above technique was added to perform a primary reaction.

The plate was washed three times with PBST.

The anti-chicken IgM/HRP was added to perform a secondary reaction.

The plate was washed three times with PBST.

TMB was added to perform a color development reaction.

1N sulfuric acid was added to stop the color development reaction.

The color was measured at $OD_{450}$.

(2) Results

The results are as shown in Table 1. The clones 2-1, 2-3 and 2-5 were specifically bound to the antigen [E2/anti-E2 antibody (F18-3) complex](see *). On the other hand, the clones 2-2, 2-4 and 2-6 were not bound to the antigen [E2/anti-E2 antibody (F18-3) complex], but were bound to F18-3. The clones 2-1, 2-3 and 2-5 corresponded to the clones 4, 9 and 46 in Example 1, respectively. The clones 2-2, 2-4 and 2-6 corresponded to the clones 8, 34 and 77 in Example 1, respectively.

As described above, according to the present invention, it was confirmed that the antibody capable of specifically binding to the complex could be obtained.

TABLE 1

Evaluation of specificity of anti-E2 antibody and objective antibodies against E2/anti-E2 antibody complex

| Clone No. | Estrogen (ng/ml) | E1 | | | E2 | | |
|---|---|---|---|---|---|---|---|
| | | F18-3 | F12-33 | Anti-AFP | F18-3 | F12-33 | Anti-AFP |
| 2-1 | 1 | 0.13 | 0.07 | 0.11 | 3.64* | 0.07 | 0.09 |
| | 0 | 0.14 | 0.07 | 0.11 | 0.12 | 0.07 | 0.11 |
| 2-2 | 1 | 0.54 | 0.07 | 0.1 | 0.52 | 0.07 | 0.1 |
| | 0 | 0.56 | 0.07 | 0.09 | 0.65 | 0.07 | 0.09 |
| 2-3 | 1 | 0.18 | 0.07 | 0.1 | 4.2* | 0.07 | 0.09 |
| | 0 | 0.23 | 0.08 | 0.1 | 0.2 | 0.07 | 0.1 |
| 2-4 | 1 | 0.38 | 0.07 | 0.1 | 0.37 | 0.07 | 0.09 |
| | 0 | 0.51 | 0.08 | 0.1 | 0.43 | 0.07 | 0.14 |
| 2-5 | 1 | 0.12 | 0.08 | 0.09 | 1.1* | 0.07 | 0.09 |
| | 0 | 0.13 | 0.07 | 0.1 | 0.14 | 0.07 | 0.11 |
| 2-6 | 1 | 0.32 | 0.07 | 0.11 | 0.24 | 0.07 | 0.11 |
| | 0 | 0.33 | 0.07 | 0.1 | 0.27 | 0.07 | 0.09 |
| Positive control | 1 | 4.72 | 4.59 | 4.33 | 4.21 | 4.6 | 3.94 |
| | 0 | 4.36 | 6 | 4.33 | 4.32 | 3.6 | 4.24 |
| Buffer | 1 | 0.13 | 0.07 | 0.1 | 0.08 | 0.07 | 0.1 |
| | 0 | 0.11 | 0.07 | 0.11 | 0.09 | 0.07 | 0.11 |

The positive control is an anti-murine antibody chicken IgM antibody.
*Remarkable increase in OD values was observed in the presence of E2.

Example 3

Evaluation of Specificity of Objective Antibody Against E2

(1) Method

The specificity of the objective antibody against E2 was evaluated by performing ELISA using the following procedure.

An E2/BSA (bovine serum albumin) complex at each concentration was added to an assay plate, and immobilized by incubating the plate at 37° C. for one hour. A reason why not E2 but the E2/BSA complex was used is that E2 is a low molecular compound and E2 alone is not absorbed onto the assay plate.

The plate was washed three times with PBST.

The plate was blocked with 1% skim milk/PBS.

The plate was washed three times with PBST.

25 μL each of E2 (100 ng/mL) or the buffer alone was added.

25 μL of the culture supernatant of the clones (2-1, 2-2, 2-3, 2-4, 2-5 and 2-6) established in Example 1 and evaluated in Example 2 was added thereto to perform a primary reaction.

The plate was washed three times with PBST.

The anti-chicken IgM-HRP was added to perform a secondary reaction.

The plate was washed three times with PBST.

TMB was added to perform a color development reaction.

1N sulfuric acid was added to stop the color development reaction.

The color was measured at $OD_{450}$.

(2) Results

The results are as shown in Table 2. No clone that was positive was found in ELISA where E2 (E2/BSA) alone was immobilized. Therefore, it is thought that the clones 2-1, 2-2, 2-3, 2-4, 2-5 and 2-6 do not produce the antibody capable of binding to E2.

TABLE 2

Evaluation of specificity of objective antibody against E2.

| E2-BSA (μg/ml) | 2-1 | | 2-2 | | 2-3 | | F16-3 | |
|---|---|---|---|---|---|---|---|---|
| | E2(−) | E2(+) | E2(−) | E2(+) | E2(−) | E2(+) | E2(−) | E2(+) |
| 9 | 0.06 | 0.07 | 0.07 | 0.06 | 0.06 | 0.07 | 4.43 | 2.72 |
| 3 | 0.07 | 0.06 | 0.07 | 0.06 | 0.06 | 0.06 | 4.76 | 0.83 |
| 1 | 0.06 | 0.06 | 0.06 | 0.06 | 0.06 | 0.06 | 4.29 | 0.29 |
| 0 | 0.06 | 0.06 | 0.06 | 0.06 | 0.06 | 0.06 | 0.06 | 0.06 |

| E2-BSA (μg/ml) | 2-4 | | 2-5 | | 2-6 | | Buffer | |
|---|---|---|---|---|---|---|---|---|
| | E2(−) | E2(+) | E2(−) | E2(+) | E2(−) | E2(+) | E2(−) | E2(+) |
| 9 | 0.06 | 0.06 | 0.06 | 0.06 | 0.06 | 0.06 | 0.06 | 0.06 |
| 3 | 0.06 | 0.07 | 0.06 | 0.06 | 0.06 | 0.06 | 0.06 | 0.06 |
| 1 | 0.06 | 0.06 | 0.06 | 0.06 | 0.06 | 0.06 | 0.06 | 0.06 |
| 0 | 0.06 | 0.06 | 0.06 | 0.06 | 0.06 | 0.06 | 0.07 | 0.06 |

Example 4

Evaluation of Cross-Reactivity to Analogous Substance (1) Method

A cross-reactivity of the antibody to an analogous substance was evaluated by performing ELISA using the following procedure.

- 5 μg/mL of the anti-E2 antibody (F18-3) was immobilized.
- The plate was washed three times with PBST.
- The plate was blocked with 1% skim milk/PBS.
- The plate was washed three times with PBST.
- E1, E2 or E3 was prepared at each concentration and 25 μg/mL thereof was added.
- Each 25 μg/mL of three culture supernatants containing the antibody (clones 2-1, 2-3 or 2-5) was added to perform a primary reaction.
- The plate was washed three times with PBST.
- The anti-chicken IgM/HRP was added to perform a secondary reaction.
- The plate was washed three times with PBST.
- TMB was added to perform a color development reaction.
- 1N sulfuric acid was added to stop the color development reaction.
- The color was measured at $OD_{450}$.

(2) Results

The results are as shown in Table 3. In Table 3, the cross-reactivity (%) was calculated based on a binding rate of the antibody of the present invention to each factor that constitutes the affinity complex or the analogous factor thereto when a binding rate of the antibody of the present invention to the objective affinity complex was calculated to be 100%. Three types of the antibodies (clones 2-1, 2-3 and 2-5) were scarcely bound to E1 and E3.

TABLE 3

Evaluation of cross-reactivity to analogous substance.

| | 2-1 | | 2-3 | | 2-5 | |
|---|---|---|---|---|---|---|
| | E1 | E3 | E1 | E3 | E1 | E3 |
| Cross-reactivity (%) | 0.05% | 0.1% | 0.05% | 0.1% | <0.05% | <0.05% |

As described above, it was shown that three types of the antibodies (clones 2-1, 2-3 and 2-5) could be specifically bound to the antigen/antibody complex [complex comprising E2/anti-E2 antibody (F18-3)]. Therefore, it was demonstrated by the present invention that it was possible to develop the antibody capable of specifically binding to the affinity complex. It was also demonstrated that it was possible to measure the small substance by the sandwich method.

Example 5

Production of Recombinant Type I Chimera Antibody

The chicken IgM antibody was converted to a murine IgG antibody to produce a recombinant type I chimera antibody. The recombinant type I chimera antibody is an antibody in which murine constant regions (CH, CL) are linked at downstream of μ and λ chain variable regions (VH and VL) of the chicken IgM antibody against the E2/anti-E2 antibody complex [heavy chain: VH derived from the chicken IgM (μ chain) and CH derived from the murine IgG1 (γ1 chain); light chain: VL derived from the chicken IgM (λ chain) and CL derived from the murine IgG (κ chain)]. Hereinafter, this antibody is referred to as a "chimera type I (antibody)" as needed.

(1) Production of Expression Vector for Chimera Type I Heavy Chain

An expression vector for the chimera type I heavy chain was produced by the following procedure.

(a) PCR was performed with μ chain cDNA of the chicken IgM antibody bound to the E2/anti-E2 antibody complex (clone 2-3) as a template using a primer A and a primer B to amplify a chicken μ chain variable region.

(b) PCR was performed with γ chain cDNA of an anti-TNF murine IgG1 antibody as a template using a primer C and a primer D to amplify a murine IgG1 constant region.

(c) Assemble PCR was performed with a mixture of the DNA fragments amplified in (a) and (b) as a template using the primer A and the primer D to prepare one DNA fragment in which the chicken μ chain variable region is linked to the murine IgG1 γ chain constant region.

(d) The DNA fragment obtained in (c) was treated with restriction enzymes HindIII and NotI, and subsequently inserted to a HindIII/NotI site of a commercially available expression vector (Invitrogen) pcDNA3.1.

(2) Production of Expression Vector for Chimera Type I Light Chain

An expression vector for the chimera type I light chain was produced by the following procedure.

(e) PCR was performed with λ chain cDNA of the chicken IgM antibody bound to the E2/anti-E2 antibody complex (clone 2-3) as the template using a primer E and a primer F to amplify a chicken λ chain variable region.

(f) PCR was performed with κ chain cDNA of the anti-TNF murine IgG1 antibody as the template using a primer G and a primer H to amplify a murine κ chain constant region.

(g) Assemble PCR was performed with a mixture of the DNA fragments amplified in (e) and (f) as the template using the primer E and the primer H to prepare one DNA fragment in which the chicken λ chain variable region is linked to the murine κ chain constant region.

(h) The DNA fragment obtained in (g) was treated with the restriction enzymes HindIII and NotI, and subsequently inserted to a HindIII/NotI site of a commercially available expression vector (Invitrogen) pcDNA3.1/Zeo.

(3) Production of Recombinant Chimera Type I Antibody and Confirmation of its Expression A recombinant chimera type I antibody was produced by the following procedure.

(i) *Escherichia coli* colonies transformed with the expression vector for the chimera type I heavy chain and the expression vector for the chimera type I light chain were cultured respectively with shaking at 37° C. overnight in 150 mL of LB medium containing 100 µg/mL of ampicillin. Subsequently, plasmids were prepared using Plasmid Midi Kit from Qiagen.

(j) CHO cells at $10^6$ cells were transformed with each 4 µg of the expression vector for the chimera type I heavy chain and the expression vector for the chimera type I light chain prepared in (i) using Lipofectamine 2000 from Invitrogen.

(k) The CHO cells transformed in (j) were cultured in Ham F-12 medium containing 10% fetal calf serum in a $CO_2$ incubator at 37° C. for 24 hours.

(l) To confirm the expression of the chimera type I antibody, it was confirmed by ELISA whether the chimera type I antibody was secreted in the culture supernatant in (k) or not. That is, the anti-murine IgG was immobilized onto an ELISA plate (Nunc), the culture supernatant diluted to (½)n was reacted thereto, and then the reaction was detected by a POD-labeled anti-murine IgG (DAKO). A murine monoclonal antibody (anti TNF36) was used as a positive control, and a CHO culture supernatant was used as a negative control. As a result, the expression of the chimera type I antibody was confirmed (Table 4).

TABLE 4

Confirmation of secretion and expression of recombinant chimera type I molecule
Result of ELISA for measuring antibody concentration

| Serial dilution of culture supernatant | Chimera type I antibody | Control murine antibody | CHO culture supernatant |
|---|---|---|---|
| x1 | 2.298 | 4.110 | 0.273 |
| x2 | 1.490 | 4.065 | 0.268 |
| x4 | 0.975 | 3.919 | 0.249 |
| x8 | 0.592 | 2.306 | 0.213 |
| x16 | 0.406 | 1.367 | 0.199 |
| x32 | 0.268 | 0.900 | 0.182 |

Example 6

Production of Recombinant Chimera Type II Antibody

The chicken IgM antibody was converted to the murine IgG antibody to produce a recombinant chimera type II antibody. The recombinant chimera type II antibody is an antibody in which a region subsequent to a hinge region (hinge region, CH2 and CH3) of the murine IgG1 is linked at downstream of the λ chain (VL and CL) and µ chain variable region (VH) and a CH1 domain of the chicken IgM antibody against the E2/anti-E2 antibody complex [heavy chain: VH and CH1 derived from chicken IgM (µ chain) and the hinge region, CH2 and CH3 derived from murine IgG1 (γ1 chain); light chain: VL and CL derived from chicken IgM (λ chain)]. Hereinafter, this antibody is referred to as a "chimera type II (antibody)" as needed.

(1) Production of Expression Vector for Chimera Type II Heavy Chain

An expression vector for the chimera type II heavy chain was produced by the following procedure.

(a') PCR was performed with µ chain cDNA of the chicken IgM antibody bound to the E2/anti-E2 antibody complex (clone 2-3) as the template using a primer I and a primer J to amplify the chicken µ chain variable region and CH1.

(b') PCR was performed with γ chain cDNA of the anti-TNF murine IgG1 antibody as the template using a primer K and the primer D to amplify the region subsequent to the hinge region (hinge region, CH2 and CH3) of the murine γ chain.

(c') Assemble PCR was performed with a mixture of the DNA fragments amplified in (a') and (b') as the template using the primer I and the primer D to prepare one DNA fragment in which the chicken µ chain variable region and CH1 were linked to the region subsequent to the hinge region (hinge region, CH2 and CH3) of the murine γ chain.

(d') The DNA fragment obtained in (c') was treated with the restriction enzymes NheI and NotI, and subsequently inserted to a NheI/NotI site of the expression vector pcDNA3.1 commercially available from Invitrogen.

(2) Production of Expression Vector for Chimera Type II Light Chain

An expression vector for the chimera type II light chain was produced by the following procedure.

(e') PCR was performed with λ chain cDNA of the chicken IgM antibody bound to the E2/anti-E2 antibody complex (clone 2-3) as the template using the primer E and a primer L to amplify the chicken λ chain.

(f') The DNA fragment amplified in (e') was treated with HindIII and NotI, and subsequently inserted to the HindIII/NotI site of the expression vector pcDNA3.1/Zeo commercially available from Invitrogen.

(3) Production of Recombinant Chimera Type II Antibody and Confirmation of its Expression The recombinant chimera type II antibody was produced by the following procedure.

(g') *Escherichia coli* colonies transformed with the expression vector for the chimera type II heavy chain and the expression vector for the chimera type II light chain were cultured respectively with shaking at 37° C. overnight in 150 mL of LB medium containing 100 µg/mL of ampicillin. Subsequently, plasmids were prepared using Plasmid Midi Kit from Qiagen.

(h') CHO cells at $10^6$ cells were transformed with each 4 µg of the expression vector for the chimera type II heavy chain and the expression vector for the chimera type II light chain prepared in (g') using Lipofectamine 2000 from Invitrogen.

(i') The CHO cells transformed in (h') were cultured in Ham F-12 medium containing 10% fetal calf serum in a $CO_2$ incubator at 37° C. for 24 hours.

(j') To confirm the expression of the chimera type II antibody, it was confirmed by ELISA whether the chimera type II antibody was secreted in the culture supernatant in (i') or not. That is, the anti-murine IgG was immobilized onto an ELISA plate (Nunc), the culture supernatant diluted to (½)n was reacted thereto, and then the reaction was detected by the POD-labeled anti-murine IgG (DAKO). The murine monoclonal antibody (anti TNF36) was used as the positive control, and the CHO culture supernatant was used as the negative control. As a result, the expression of the chimera type II antibody was confirmed (Table 5).

TABLE 5

Confirmation of secretion and expression of
recombinant chimera type II molecule
Result of ELISA for measuring antibody concentration

| Serial dilution of culture supernatant | Chimera type II antibody | Control murine antibody | CHO culture supernatant |
|---|---|---|---|
| x1 | 3.508 | 4.110 | 0.273 |
| x2 | 3.339 | 4.065 | 0.268 |
| x4 | 3.081 | 3.919 | 0.249 |
| x8 | 2.173 | 2.306 | 0.213 |
| x16 | 1.489 | 1.367 | 0.199 |
| x32 | 1.015 | 0.900 | 0.182 |

TABLE 6

Primers used for production of chimera type I
antibody and chimera type II antibody

| Name | Nucleotide sequence | SEQ ID NO |
|---|---|---|
| Primer A | CAGCAGCAGAAGCTTCCACCATGAGCCCACTCGTCTCCTCCCT | SEQ ID NO: 1 |
| Primer B | TCGTTTTGGCGGAGGAGACGATGACTTCGGT | SEQ ID NO: 2 |
| Primer C | CGTCTCCTCCGCCAAAACGACACCCCCATC | SEQ ID NO: 3 |
| Primer D | CAGCAGCAGGCGGCCGCTCATTTACCAGGAGAGTGGGAGAG | SEQ ID NO: 4 |
| Primer E | CAGCAGCAGAAGCTTCCACCATGGCCTGGGCTCCTCTCCTCCTG | SEQ ID NO: 5 |
| Primer F | CAGCATCAGCACCTAGGACGGTCAGGGTTGT | SEQ ID NO: 6 |
| Primer G | CGTCCTAGGTGCTGATGCTGCACCAACTGT | SEQ ID NO: 7 |
| Primer H | CAGCAGCAGGCGGCCGCCTAACACTCATTCCTGTTGAAGCT | SEQ ID NO: 8 |
| Primer I | CAGCAGCAGGCTAGCCCACCATGAGCCCACTCGTCTCCTCCCT | SEQ ID NO: 9 |
| Primer J | ACAACCACAATCCCTGGGCACGGGAATCGGGGGACCTGGGTT | SEQ ID NO: 10 |
| Primer K | AACCCAGGTCCCCCGATTCCCGTGCCCAGGGATTGTGGTTGT | SEQ ID NO: 11 |
| Primer L | CTGCTGCTGGCGGCCGCTTAGCACTCGGACCTCTTCAGGGT | SEQ ID NO: 12 |

Example 7

Acquisition of Antibody Against Affinity Complex
(T3/Anti-T3 Antibody Complex)

An antibody against a T3/anti-T3 antibody complex was acquired by performing the following method using in vitro chicken IgM acquisition technology (ADLib system). Hereinafter, diiodothyronine, triiodothyronine, and thyroxine are sometimes abbreviated as T2, T3, and T4, respectively. Also hereinafter, 1 µg/mL of T3 corresponds to 1.5 µM, 1 µg/mL of a T3-92 antibody corresponds to 6.7 nM, and 1 µg/mL of a T3-31 antibody corresponds to 6.7 nM.

(1) Diversification of Chicken B Cell Line DT40 Library

The diversified DT40 cells were prepared by the procedure in Example 1 (1).

(2) Passage of DT40 Library

Passage of a DT40 library was performed by the procedure in Example 1 (2).

(3) Preparation of Antigen Binding Particles

Antigen binding particles were prepared by the following procedure.

300 µg/mL of the anti-T3 antibody (T3-92) was added to magnetic particles to which protein G had been immobilized.

T3-92 was immobilized by reacting at 4° C. for one hour.
The particles were washed four times with 0.1% BSA/PBS.
The particles were dispersed in PBS containing 300 µg/mL of T3.
An antigen/antibody complex was formed by reacting at 4° C. for one hour.
The particles were washed four times with 0.1% BSA/PBS.

(4) Culture of Cells Producing Objective Antibody

Cells producing the objective antibody were cultured by the following procedure.

50 mL of the CS$^+$ medium was added to two 15 cm dishes. Cells at $1.5 \times 10^7$ were added thereto and cultured for one day.

The cell suspension was transferred to a 50 mL tube, and centrifuged at 4° C. at 1,000 rpm for 10 minutes.
After removing a supernatant, the cells were washed twice with 1% BSA/PBS and transferred to a 1.5 mL tube.
The tube was centrifuged at 4° C. at 3,500 rpm for 5 minutes, and a supernatant was removed.
The antigen binding particles prepared in (3) were washed four times with 1% BSA/PBS.
The cells and the antigen binding particles were mixed and reacted at 4° C. for 30 minutes.
The mixture was washed five times with 1% BSA/PBS, and excess cells were removed.
The cells/particles were dispersed in the CS$^-$ medium.
The cells/particles were seeded in a 96-well plate, and cultured for a week.

(5) Selection of Cells Producing Objective Antibody

The selection was performed by an antigen/antibody complex-immobilized ELISA. By the difference in color development in the presence or absence of T3, it was evaluated whether the cell produced the objective antibody or not. The procedure was as follows.

1 µg/mL of the anti-T3 antibody was added and immobilized to an assay plate.

The plate was washed three times with PBST.
The plate was blocked with 1% BSA/PBS.
The plate was washed three times with PBST.
50 μL of T3 (50 ng/mL) or the buffer alone was added and T3 was bound to the immobilized antibody.
The plate was washed three times with PBST.
50 μL of a DT40 culture supernatant was added to perform a primary reaction.
The plate was washed three times with PBST.
The anti-chicken IgM/HRP was added to perform a secondary reaction.
The plate was washed three times with PBST.
TMB was added to perform a color development reaction.
1N sulfuric acid was added to stop the color development reaction.
The color was measured at OD450.

1N sulfuric acid was added to stop the color development reaction.
The color was measured at OD450.
(2) Results
The results are as shown in Table 7. Clones 6-19, 5-3, 5-6, 5-13, and 5-22 were specifically bound to the antigen [T3/anti-T3 antibody (T3-92) complex](see*). A clone 5-33 was weakly cross-reacted to the T2/anti-T3 antibody (T3-92) complex. When the clone 5-33 was used as a detection antibody, the cross-reactivity to T2 was observed, suggesting that the immobilized antibody T3-92 was weakly cross-reacted to T2. Meanwhile, a clone 5-32 was bound to not only the antigen [T3/anti-T3 antibody (T3-92) complex] but also the T3-92 antibody. The clone 5-32 was not bound to the T3-31 antibody, and thus, was the clone specifically bound to the T3-92 antibody. The clones 6-19, 5-3, 5-6, 5-13 and 5-22 correspond to the clones 23, 91, 94, 101 and 110 in Example 7, respectively. The clone 5-33 corresponds to the clone 121 in Example 7, and the clone 5-32 corresponds to the clone 120 in Example 7.

TABLE 7

Evaluation of specificity of objective antibodies against anti-T3 antibody and T3/anti-T3 antibody complex

| Immobilized antibody | Antigen | Detection antibody | | | | | | |
|---|---|---|---|---|---|---|---|---|
| | | 6-19 | 5-3 | 5-6 | 5-13 | 5-22 | 5-33 | 5-32 |
| T3-92 | T3 | 3.18* | 3.369* | 3.507* | 3.18* | 3.452* | 2.734* | 3.45 |
| | T2 | 0.16 | 0.27 | 0.24 | 0.20 | 0.30 | 1.30 | 3.11 |
| | T4 | 0.26 | 0.21 | 0.17 | 0.17 | 0.23 | 0.19 | 3.31 |
| | — | 0.17 | 0.18 | 0.18 | 0.15 | 0.17 | 0.15 | 3.33 |
| T3-31 | T3 | 0.12 | 0.12 | 0.10 | 0.08 | 0.10 | 0.10 | 0.09 |
| | T2 | 0.12 | 0.13 | 0.11 | 0.14 | 0.11 | 0.10 | 0.10 |
| | T4 | 0.11 | 0.12 | 0.10 | 0.19 | 0.10 | 0.10 | 0.09 |
| | — | 0.13 | 0.13 | 0.10 | 0.10 | 0.11 | 0.10 | 0.09 |
| AFP-U119 | T3 | 0.12 | 0.12 | 0.10 | 0.13 | 0.10 | 0.09 | 0.10 |
| | — | 0.12 | 0.12 | 0.10 | 0.10 | 0.10 | 0.08 | 0.10 |

AFP-U119 (negative control) is an anti-AFP murine antibody.

Figure 3:
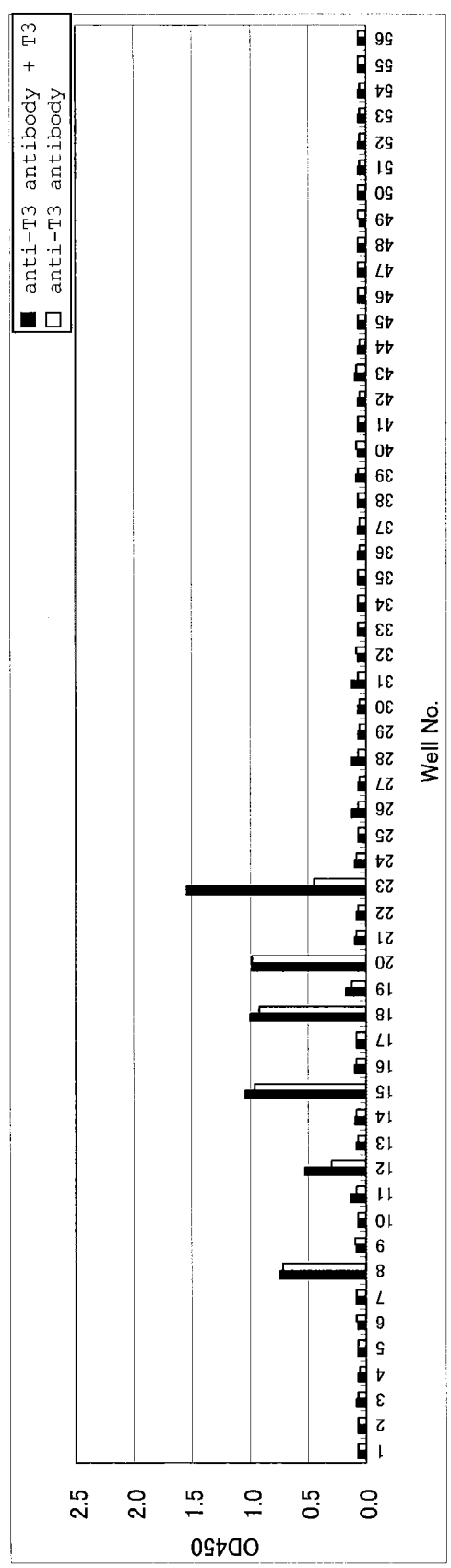
FIG. 3 is a view showing cell clones (No. 1 to 56) obtained by the method of the present invention. One type of cell clone produced an antibody capable of specifically binding to an antigen/antibody complex (affinity complex comprising T3 and an anti-T3 antibody)
Figure 4:
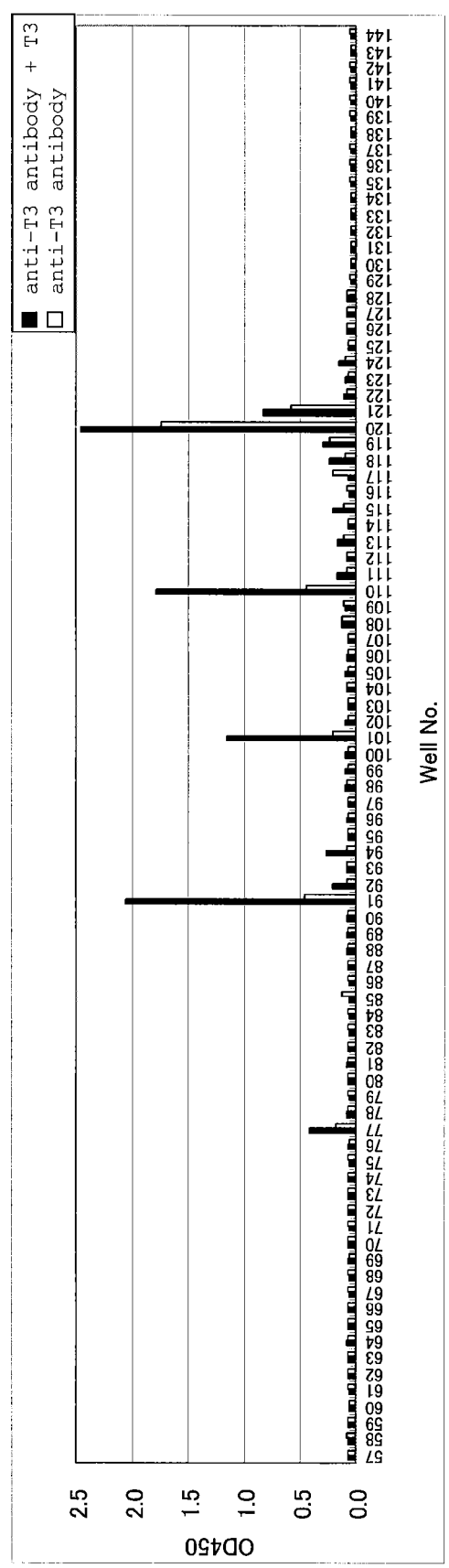
FIG. 4 is a view showing cell clones (No. 57 to 144) obtained by the method of the present invention. Five types of cell clones produced an antibody capable of specifically binding to the antigen/antibody complex (affinity complex comprising T3 and the anti-T3 antibody)

(6) Results
Clones (Well No. 23, 91, 94, 101, 110, 121) having a remarkable difference in reactivity in the absence or presence of T3 (50 ng/mL) were successfully obtained at high rate (6 clones/144=4.2%, see FIGS. 3 and 4).

Example 8

Evaluation of Specificity of Affinity Complex (T3/Anti-T3 Antibody Complex) Antibody (1) Method
The specificity was evaluated by ELISA using the following procedure.
2 μg/mL of two types of the anti-T3 antibodies (T3-92, T3-31), or the anti-AFP antibody was immobilized to an assay plate.
The plate was washed three times with PBST.
The plate was blocked with 1% BSA/PBS.
The plate was washed three times with PBST.
T3, T2 and T4 were prepared at 100 ng/mL, and each 50 μL thereof was added to the plate and incubated.
The plate was washed three times with PBST.
50 μL of the antibody from each clone established by the above technique was added to the plate, and incubated.
The plate was washed three times with PBST.
The anti-chicken IgM/HRP was added and incubated.
The plate was washed three times with PBST.
TMB was added to perform a color development reaction.

Example 9

Evaluation of Specificity of Objective Antibody Against T3

(1) Method
The specificity of the objective antibody against T3 was evaluated by performing ELISA using the following procedure.
5 μg/mL of a T3/BSA conjugate was immobilized to an assay plate.
The plate was washed three times with PBST.
The plate was blocked with 1% BSA/PBS.
The plate was washed three times with PBST.
50 μL of each clone as the antibody established by the above technique was added to the plate to perform a primary reaction.
The plate was washed three times with PBST.
The anti-chicken IgM/HRP was added to perform a secondary reaction.
When the murine antibody was used for the primary reaction, an anti-mouse Ig/HRP was added to perform the secondary reaction.
The plate was washed three times with PBST.
TMB was added to perform a color development reaction.
1N sulfuric acid was added to stop the color development reaction.
The color was measured at OD450.

(2) Results

The results are as shown in Table 8. No positive clone was found in ELISA in which T3 (T3/BSA) alone had been immobilized. Therefore, it is thought that the clones 6-19, 5-3, 5-6, 5-13, 5-22, and 5-33 do not produce the antibody capable of binding to T3.

TABLE 8

Evaluation of specificity of objective antibodies against T3

| Clone No. | $OD_{450}$ |
|---|---|
| 6-19 | 0.12 |
| 5-3 | 0.13 |
| 5-6 | 0.11 |
| 5-13 | 0.10 |
| 5-22 | 0.11 |
| 5-33 | 0.11 |
| 5-32 | 0.11 |
| T3-92 | 3.37 |
| T3-31 | 3.30 |
| AFP-U119 | 0.17 |
| (—) | 0.10 |

T3-92 and T3-31 (positive controls) are murine anti-T3 antibodies.
AFP-U119 (negative control) is a murine anti-AFP antibody.

Example 10

Evaluation of Cross-Reactivity to Analogous Substance (1) Method

The cross-reactivity of the antibody to the analogous substance was evaluated by performing ELISA using the following procedure.

2 μg/mL of the anti-T3 antibody (T3-92) was immobilized to an assay plate.
  The plate was washed three times with PBST.
  The plate was blocked with 1% BSA/PBS.
  The plate was washed three times with PBST.
  T3, T2 and T4 were prepared at each concentration, and each 50 μL thereof was added to the plate and incubated.
  The plate was washed three times with PBST.
  50 μL of each clone as the antibody established by the above technique was added to the plate, and incubated.
  The plate was washed three times with PBST.
  The anti-chicken IgM/HRP was added and incubated.
  The plate was washed three times with PBST.
  TMB was added to perform a color development reaction.
  1N sulfuric acid was added to stop the color development reaction.
  The color was measured at OD450.

(2) Results

The results are as shown in Table 9. The cross-reactivity was calculated based on the binding rate of the antibody of the present invention to each factor that constitutes the affinity complex or the analogous factor thereto when the binding rate of the antibody of the present invention to the objective affinity complex was calculated to be 100%. Five types of antibodies (clones 5-3, 5-6, 5-13, 6-19 and 5-22) were scarcely bound to T2 and T4. When the clone 5-33 was used for the detection antibody, the weak cross-reactivity to T2 was observed. This result indicates that the immobilized antibody T3-92 is also cross-reactive to T2 and that the five types of the antibodies (clones 5-3, 5-6, 5-13, 6-19 and 5-22) discriminate the affinity complex from the analogous affinity complex.

TABLE 9

Evaluation of cross-reactivity to analogous substances

| Cross-reactivity (%) | 5-3 | 5-6 | 5-13 | 6-19 | 5-22 | 5-33 |
|---|---|---|---|---|---|---|
| T2 | 0.001 | 0.019 | 0.031 | 0.002 | 0.154 | 1.23 |
| T4 | 0.167 | 0.278 | 0.278 | 0.278 | 0.278 | 0.154 |

As described above, it was shown that the five types of the antibodies (clones 5-3, 5-6, 5-13, 5-22 and 6-19) could be specifically bound to the antigen/antibody complex [complex comprising T3/anti-T3 antibody (T3-92)]. Therefore, it was demonstrated by the present invention that it was possible to develop the antibody capable of specifically binding to the affinity complex. It was also demonstrated that it was possible to measure the small substance by the sandwich method.

Example 11

Evaluation of Sensitivity to T3

(1) Method

The sensitivity to T3 was evaluated by ELISA using the following procedure.

2 μg/mL of the anti-T3 antibody (T3-92) was immobilized to an assay plate.
  The plate was washed three times with PBST.
  The plate was blocked with 1% BSA/PBS.
  The plate was washed three times with PBST.
  T3 was prepared at each concentration, and each 50 μL thereof was added to the plate and incubated.
  The plate was washed three times with PBST.
  50 μL of the antibody established by the above technique was added to the plate, and incubated.
  The plate was washed three times with PBST.
  The anti-chicken IgM/HRP was added and incubated.
  The plate was washed three times with PBST.
  TMB was added to perform a color development reaction.
  1N sulfuric acid was added to stop the color development reaction.
  The color was measured at OD450.

(2) Results

Figure 5:
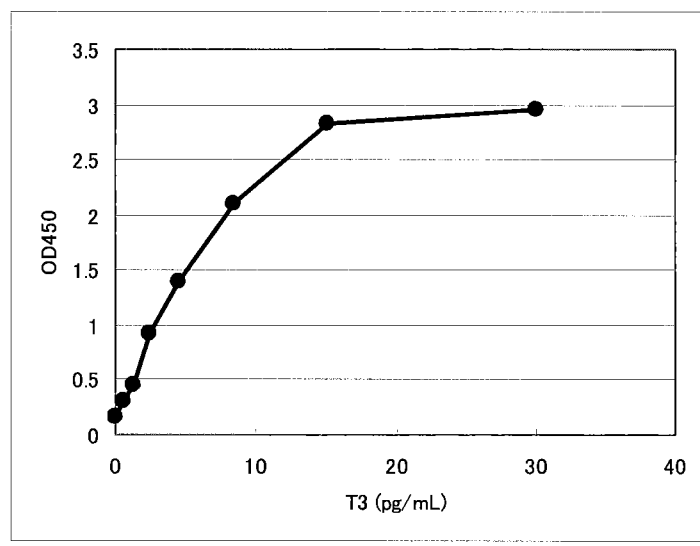
FIG. 5 is a view showing a sensitivity to T3 in the measurement using the antibody of the present invention.

The results are as shown in Table 10 and FIG. 5. T3 at a concentration of 1 pg/mL or less could be detected by the sandwich method using the produced antibody (clone 5-3-1). The clone 5-3-1 corresponds to the clone 5-3 in Example 7.

TABLE 10

Evaluation of sensitivity to T3

| T3 (pg/ml) | $OD_{450}$ 5-3-1 |
|---|---|
| 30 | 2.96 |
| 15.16 | 2.82 |
| 8.37 | 2.11 |
| 4.55 | 1.40 |
| 2.44 | 0.92 |
| 1.22 | 0.46 |
| 0.61 | 0.32 |
| 0 | 0.16 |

Example 12

Acquisition of Antibody Against Affinity Complex [25OH Vitamin D3/Anti-25OH Vitamin D Antibody Complex]

An antibody against a 25OH vitamin D3/anti-25OH vitamin D antibody complex was acquired by performing the following method using in vitro chicken IgM acquisition technology (ADLib system). Hereinafter, 1 µg/mL of 25OH vitamin D3 corresponds to 2.5 µM, and 1 µg/mL of the anti-25OH vitamin D antibody corresponds to 6.7 nM.

(1) Diversification of Chicken B Cell Line DT40 Library

The diversified DT40 cells were prepared by the procedure in Example 1 (1)

(2) Passage of DT40 Library

Passage of DT40 cells was performed by the procedure in Example 1 (2).

(3) Preparation of Antigen Binding Particles

Antigen binding particles were prepared by the following procedure.

- 300 µg/mL of the anti-25OH vitamin D antibody was added to magnetic particles to which protein G had been immobilized.
- The antibody was immobilized by reacting at 4° C. for one hour.
- The particles were washed four times with 0.1% BSA/PBS.
- The particles were dispersed in PBS containing 300 µg/mL of 25OH vitamin D3.
- An antigen/antibody complex was formed by reacting at 4° C. for one hour.
- The particles were washed four times with 0.1% BSA/PBS.

(4) Culture of Cells Producing Objective Antibody

Cells producing the objective antibody were cultured by the following procedure.

- 50 mL of the $CS^+$ medium was added to each of two 15 cm dishes.
- Cells at $1.5 \times 10^7$ cells were added thereto and cultured for one day.
- The cell suspension was transferred to a 50 mL tube, and centrifuged at 4° C. at 1,000 rpm for 10 minutes.
- After removing a supernatant, the cells were washed twice with 1% BSA/PBS and transferred to a 1.5 mL tube.
- The tube was centrifuged at 4° C. at 3,500 rpm for 5 minutes, and a supernatant was removed.
- The antigen binding particles prepared in (3) were washed four times with 1% BSA/PBS.
- The cells and the antigen binding particles were mixed and reacted at 4° C. for 30 minutes.
- The mixture was washed five times with 1% BSA/PBS, and excess cells were removed.
- The cells/particles were dispersed in the $CS^-$ medium.
- The cells/particles were seeded in a 96-well plate, and cultured for a week.

(5) Selection of Cells Producing Objective Antibody

The selection was performed by an antigen/antibody complex-immobilized ELISA. By the difference in color development in the presence or absence of 25OH vitamin D3, it was evaluated whether the cell produced the objective antibody or not. The procedure was as follows.

- 1 µg/mL of the anti-25OH vitamin D antibody was added and immobilized to an assay plate.
- The plate was washed three times with PBST.
- The plate was blocked with 1% BSA/PBS.
- The plate was washed three times with PBST.
- 50 µL of 25OH vitamin D3 (1 µg/mL) or the buffer alone was added and 25OH vitamin D3 was bound to the immobilized antibody.
- The plate was washed three times with PBST.
- 50 µL of a DT40 culture supernatant was added to perform a primary reaction.
- The plate was washed three times with PBST.
- The anti-chicken IgM/biotin was added to perform a secondary reaction.
- The plate was washed three times with PBST.
- Streptavidin/HRP was added to perform a tertiary reaction.
- The plate was washed three times with PBST.
- TMB was added to perform a color development reaction.
- 1N sulfuric acid was added to stop the color development reaction.
- The color was measured at OD450.

(6) Results

Figure 6:
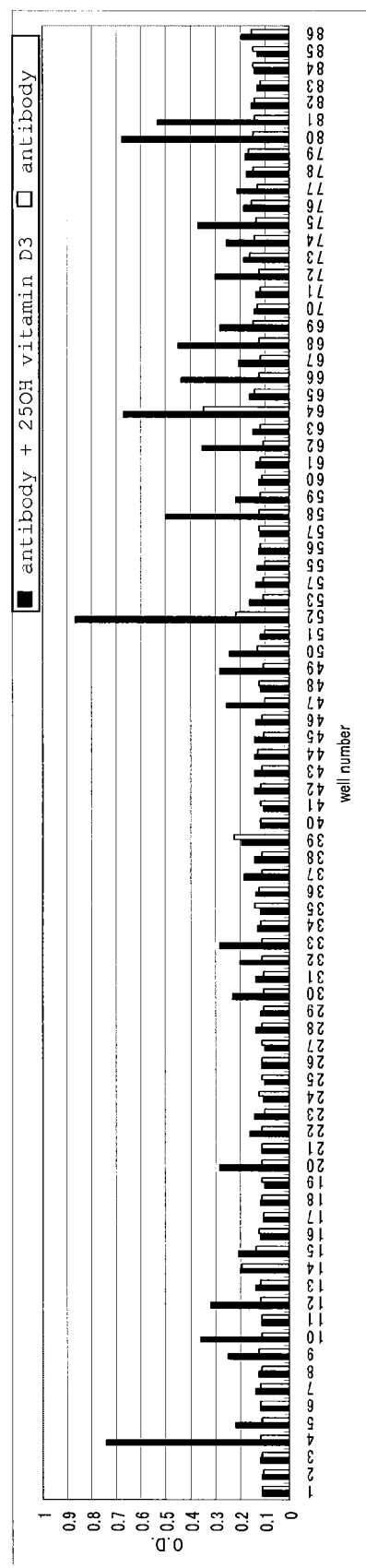
FIG. 6 is a view showing cell clones (No. 1 to 86) obtained by the method of the present invention. Four cell clones produced an antibody capable of specifically binding to an antigen/antibody complex (affinity complex comprising 25OH vitamin D3 and an anti-25OH vitamin D antibody)
Figure 7:
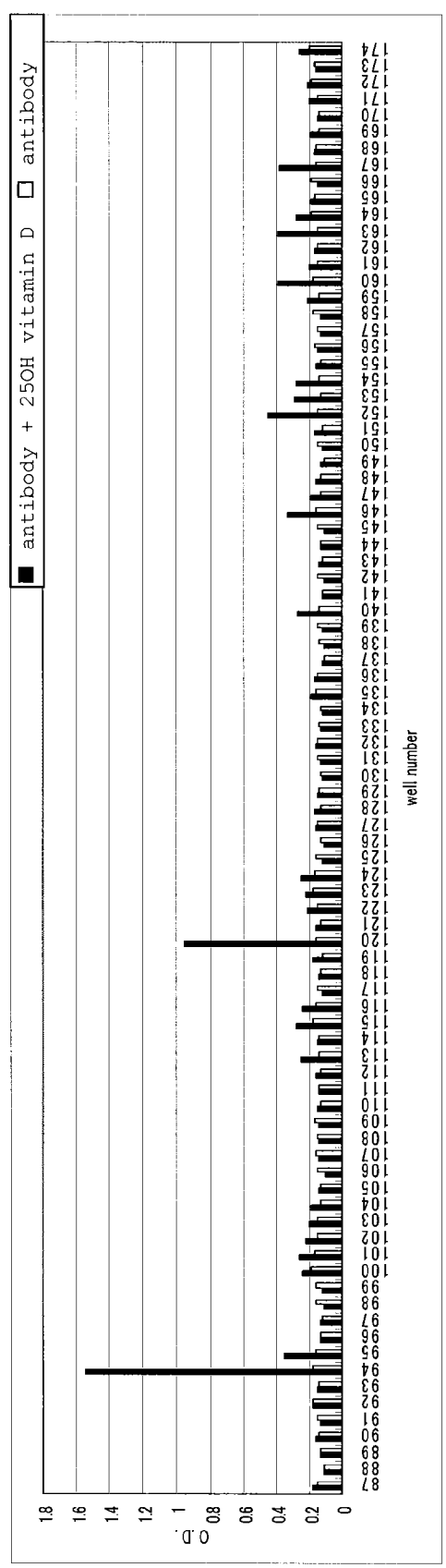
FIG. 7 is a view showing cell clones (No. 87 to 174) obtained by the method of the present invention. Two types of cell clones produced an antibody capable of specifically binding to the antigen/antibody complex (affinity complex comprising 25OH vitamin D3 and the anti-25OH vitamin D antibody)

Clones (Well No. 4, 52, 80, 81, 94, 120) exhibiting the remarkable difference in reactivity in the presence and absence of 25OH vitamin D3 (1 µg/mL) were successfully obtained at high rate (6 clones/174=3.4%, see FIGS. 6 and 7).

Example 13

Evaluation of Specificity of Affinity Complex (25OH Vitamin D3/Anti-25OH Vitamin D Antibody Complex) Antibody (1) Method The specificity was evaluated by ELISA using the following procedure.

- 1 µg/mL of the anti-25OH vitamin D3 antibody or the anti-T3 antibody was immobilized respectively to an assay plate.
- The plate was washed three times with PBST.
- The plate was blocked with 1% BSA/PBS.
- The plate was washed three times with PBST.
- 25OH vitamin D3 as well as analogous substances thereof: 25OH vitamin D2, 1,25(OH)$_2$ vitamin D3, 1,25(OH)$_2$ vitamin D2, vitamin D3 and vitamin D2, were prepared each at a concentration of 200 ng/mL, and each 50 µL thereof was added and incubated.
- The plate was washed three times with PBST.
- 50 µL of each clone as the antibody established by the above technique was added to the plate, and incubated.
- The plate was washed three times with PBST.
- The anti-chicken IgM/biotin was added to perform a secondary reaction.
- The plate was washed three times with PBST.
- Streptavidin/HRP was added to perform a tertiary reaction.
- The plate was washed three times with PBST.
- TMB was added to perform a color development reaction.
- 1N sulfuric acid was added to stop the color development reaction.
- The color was measured at OD450.

(2) Results

The results are as shown in Table 11. Clones 3-2D1-12 and 3-2D1-22 were specifically bound to the 25OH vitamin D3/anti-25OH vitamin D antibody complex and the 25OH vitamin D2/anti-25OH vitamin D antibody complex, which were used as the antigen (see *). The clones 3-2D1-12 and 3-2D1-22 were not bound to the anti-T3 antibody used as the negative control. The clones 3-2D1-12 and 3-2D1-22 correspond to subclones of the clone 4 obtained in Example 12.

TABLE 11

Evaluation of specificity of anti-25OH vitamin D antibody and objective antibody against 25OH vitamin D3/anti-25OH vitamin D antibody complex.

| Immobilized antibody | Antigen | Detection antibody 3-2D1-12 | Detection antibody 3-2D1-22 |
|---|---|---|---|
| Anti-25OH vitamin D antibody | 25OH vitamin D3 | 1.50* | 1.30* |
| | 25OH vitamin D2 | 1.63* | 1.87* |
| | 1,25(OH)$_2$ vitamin D3 | 0.14 | 0.14 |
| | 1,25(OH)$_2$ vitamin D2 | 0.13 | 0.12 |
| | Vitamin D3 | 0.08 | 0.07 |
| | Vitamin D2 | 0.09 | 0.08 |
| | — | 0.07 | 0.07 |
| Anti-T3 antibody | 25OH vitamin D3 | 0.08 | 0.07 |
| | — | 0.07 | 0.06 |

Numerical values are measured values at OD$_{450}$.

Example 14

Evaluation of Specificity of Objective Antibody Against 25OH Vitamin D3

(1) Method

The specificity of the objective antibody against 25OH vitamin D3 was evaluated by ELISA using the following procedure.

1 μg/mL of a 25OH vitamin D3/BSA conjugate was immobilized to an assay plate.
The plate was washed three times with PBST.
The plate was blocked with 1% BSA/PBS.
The plate was washed three times with PBST.
50 μL of each clone as the antibody established by the above technique was added to the plate to perform a primary reaction.
The plate was washed three times with PBST.
The anti-chicken IgM/biotin was added to perform a secondary reaction.
When the anti-25OH vitamin D antibody was used for the primary reaction, an anti-IgG/HRP was added to perform the secondary reaction.
The plate was washed three times with PBST.
Streptavidin/HRP was added to perform a tertiary reaction.
The plate was washed three times with PBST.
TMB was added to perform a color development reaction.
1N sulfuric acid was added to stop the color development reaction.
The color was measured at OD450.

(2) Results

The results are as shown in Table 12. The clones 3-2D1-12 and 3-2D1-12 did not react with immobilized 25OH vitamin D3/BSA in ELISA. This indicates that these clones are not bound to 25OH vitamin D3 alone.

TABLE 12

Evaluation of specificity of objective antibody against 25OH vitamin D3.

| Reaction antibody | OD$_{450}$ |
|---|---|
| 3-2D1-12 | 0.08 |
| 3-2D1-22 | 0.08 |
| Anti-25OH vitamin D antibody | 2.37* |
| — | 0.06 |

Reference Example 1

Confirmation of Cross-reactivity of Anti-25OH Vitamin D Antibody (1) Method

The cross-reactivity of the anti-25OH vitamin D antibody to analogous substances was evaluated by ELISA using the following procedure.

1 μg/mL of the anti-25OH vitamin D antibody was immobilized to an assay plate.
The plate was washed three times with PBST.
The plate was blocked with 1% BSA/PBS.
The plate was washed three times with PBST.
200 ng/mL of alkaline phosphatase-labeled 25OH vitamin D3 was mixed with 25OH vitamin D3, 25OH vitamin D2, 1,25-(OH)$_2$ vitamin D3, 1,25(OH)$_2$ vitamin D2, vitamin D3 or vitamin D2 prepared at each concentration, and each 50 μL of the mixture was added and incubated.
The plate was washed three times with PBST.
The plate was washed twice with MilliQ water.
PNPP was added to perform a color development reaction.
2.5 mM EDTA was added to stop the color development reaction.
The color was measured at OD405.

(2) Results

The results are as shown in Table 13. In Table 13, the cross-reactivity (%) was calculated based on the binding rate of the anti-25OH vitamin D antibody to the 25OH vitamin D3 analogous substance when the binding rate of the anti-25OH vitamin D antibody to 25OH vitamin D3 was calculated to be 100%. The anti-25OH vitamin D antibody exhibited the high cross-reactivity to 25OH vitamin D2, 1,25-(OH)$_2$ vitamin D3, and 1,25-(OH)$_2$ vitamin D2, but substantially did not exhibited the cross-reactivity to vitamin D3 and vitamin D2.

TABLE 13

Cross-reactivity of anti-25OH vitamin D antibody.

| Antigen | Cross-reactivity (%) of anti-25OH vitamin D antibody |
|---|---|
| 25OH vitamin D2 | 96.30 |
| 1,25(OH)$_2$ vitamin D3 | 73.10 |
| 1,25(OH)$_2$ vitamin D2 | >100 |
| Vitamin D3 | 2.32 |
| Vitamin D2 | 2.40 |

Example 15

Evaluation of Cross-reactivity of Objective Antibody to Analogous Substances (1) Method The cross-reactivity of the objective antibody to the analogous substances was evaluated by ELISA using the following procedure.

1 μg/mL of the anti-25OH vitamin D antibody was immobilized to an assay plate.
The plate was washed three times with PBST.
The plate was blocked with 1% BSA/PBS.
The plate was washed three times with PBST.

25OH vitamin D3, 25OH vitamin D2, 1,25-(OH)$_2$ vitamin D3 or 1,25-(OH)$_2$ vitamin D2 was prepared at each concentration, and each 50 μL thereof was added and incubated.
The plate was washed three times with PBST.
50 μL of the clone 3-2D1-12 was each added and incubated.
The plate was washed three times with PBST.
The anti-chicken IgM/biotin was added and incubated.
The plate was washed three times with PBST.
Streptavidin/HRP was added and incubated.
The plate was washed three times with PBST.
TMB was added to perform a color development reaction.
1N sulfuric acid was added to stop the color development reaction.
The color was measured at OD450.

(2) Results

The results are as shown in Table 14. In Table 14, the cross-reactivity (%) was calculated based on the binding rate of the antibody of the present invention to each factor that constitutes the affinity complex or the analogous substance thereto when the binding rate of the antibody of the present invention to the objective affinity complex (25OH vitamin D3/anti-25OH vitamin D antibody complex) was calculated to be 100%. The competitive inhibitory assay using the anti-25OH vitamin D antibody alone could not discriminate 25OH vitamin D3, 25OH vitamin D2, 1,25-(OH)$_2$ vitamin D2, and 1,25-(OH)$_2$ vitamin D3. However, 25OH vitamin D3 and 25OH vitamin D2 could be discriminated and measured by the sandwich assay using the antibody of the present invention.

TABLE 14

Cross-reactivity of objective antibody to analogous substances

| Analogous substance that constitutes affinity complex (complex of analogous substance and anti-25OH vitamin D antibody) | Cross-reactivity of 3-2D1-12 (%) |
| --- | --- |
| 25OH vitamin D2 | 100 |
| 1,25(OH)$_2$ vitamin D3 | <0.01 |
| 1,25(OH)$_2$ vitamin D2 | <0.01 |
| — | <0.01 |

Example 16

Sensitivity to 25OH Vitamin D3 in Measurement Using Objective Antibody (1) Method The sensitivity to 25OH vitamin D3 in the measurement using the objective antibody was evaluated by ELISA using the following procedure.
  1 μg/mL of the anti-25OH vitamin D antibody was immobilized to an assay plate.
  The plate was washed three times with PBST.
  The plate was blocked with 1% BSA/PBS.
  The plate was washed three times with PBST.
  25OH vitamin D3 was prepared at each concentration, and each 50 μL thereof was added and incubated.
  The plate was washed three times with PBST.
  50 μL of the clone 3-2D1-12 was each added and incubated.
  The plate was washed three times with PBST.
  The anti-chicken IgM/biotin was added and incubated.
  The plate was washed three times with PBST.
  Streptavidin/HRP was added and incubated.
  The plate was washed three times with PBST.
  TMB was added to perform a color development reaction.
  1N sulfuric acid was added to stop the color development reaction.
  The color was measured at OD450.

(2) Results

Figure 8:
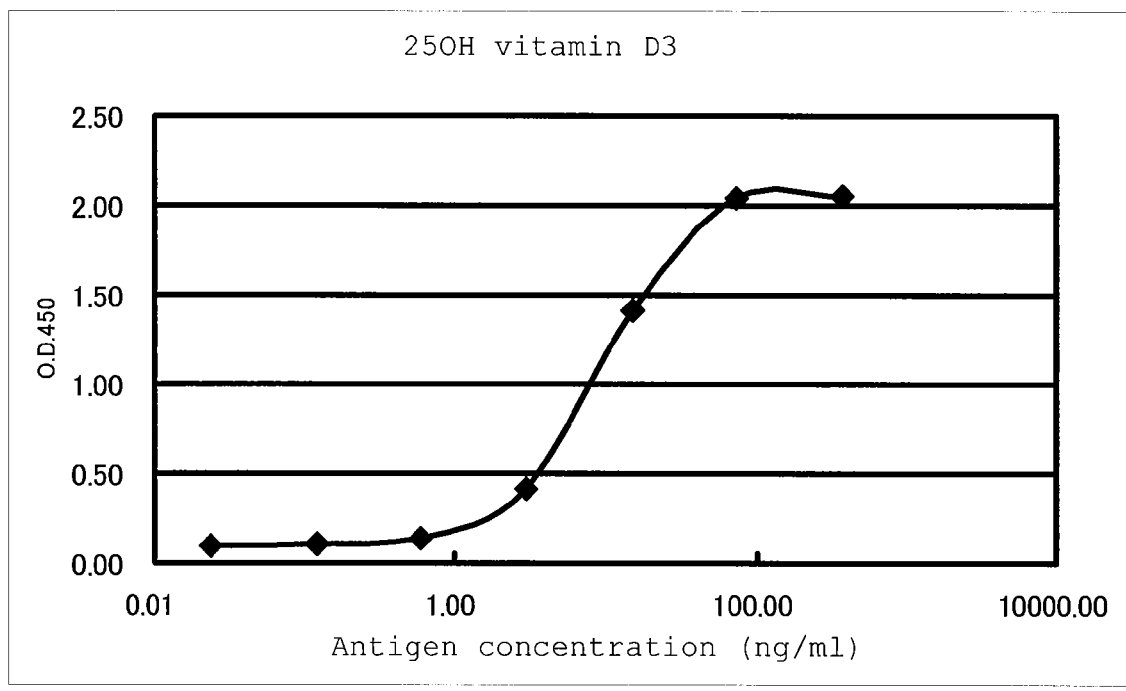
FIG. 8 is a view showing the sensitivity to 25OH vitamin D3 in the measurement using the antibody of the present invention.

The results are as shown in Table 15 and FIG. 8. By the sandwich method using the established antibody and the clone 3-2D1-12, it was possible to detect 25OH vitamin D3 at concentrations of 3 ng/mL or less.

TABLE 15

Sensitivity to 25OH vitamin D3 using objective antibody

| 25OH vitamin D3 (ng/mL) | CD$_{450}$ 3-2D1-12 |
| --- | --- |
| 370.00 | 2.05 |
| 74.00 | 2.04 |
| 14.80 | 1.41 |
| 2.96 | 0.41 |
| 0.59 | 0.14 |
| 0.12 | 0.10 |
| 0.02 | 0.10 |
| 0 | 0.11 |

Example 17

Specificity of the Antibody of the Present Invention for Complex of E2 and Anti-E2 Antibody (17-1) Evaluation of Specificity of Immobilized Antibody (Primary Antibody) by Competitive Method In order to evaluate the specificity of the antibody of the present invention, first the specificity of the primary antibody for E2 was evaluated.

(A) Method (i) Immobilization of Primary Antibody
  The anti-E2 antibody (F18-3) was immobilized by the following procedure.
    The anti-E2 antibody (0.5 μg/mL) was added to NUNC POLYSORP (96 well plate for ELISA) and incubated overnight.
    The plate to which the anti-E2 antibody had been immobilized was blocked with 5% skim milk (37° C., one hour).

(ii) ELISA
  ELISA was performed by the following procedure. E2-3 sulfate is a compound in which a hydrogen atom in a hydroxyl group at position 3 of E2 was substituted with a sulfate group.
    The antigen: E2 (diluted at 3n from 6 ng/mL) and analogous antigens: E1, E3, E2-3 sulfate (diluted at 3n from 54 ng/mL) were prepared.
    A labeled antigen: a fusion body of E2/ALP (alkaline phosphatase) at position 3 (46 ng/mL) was prepared.
    The antigen or the analogous antigen (each 50 μL) and the labeled antigen (50 μL) were added to the immobilized plate.
    The immobilized plate was incubated at 37° C. for one hour.
    The immobilized plate was washed three times with PBS/Tween 20 (0.05%).
    A color was developed with pNPP and absorbance was measured.

A reaction in the absence of the antigen or the analogous antigen was made 100%, and an inhibitory rate (% reaction) was calculated when the antigen or the analogous antigen was added at each concentration.

(B) Results

Figure 9:
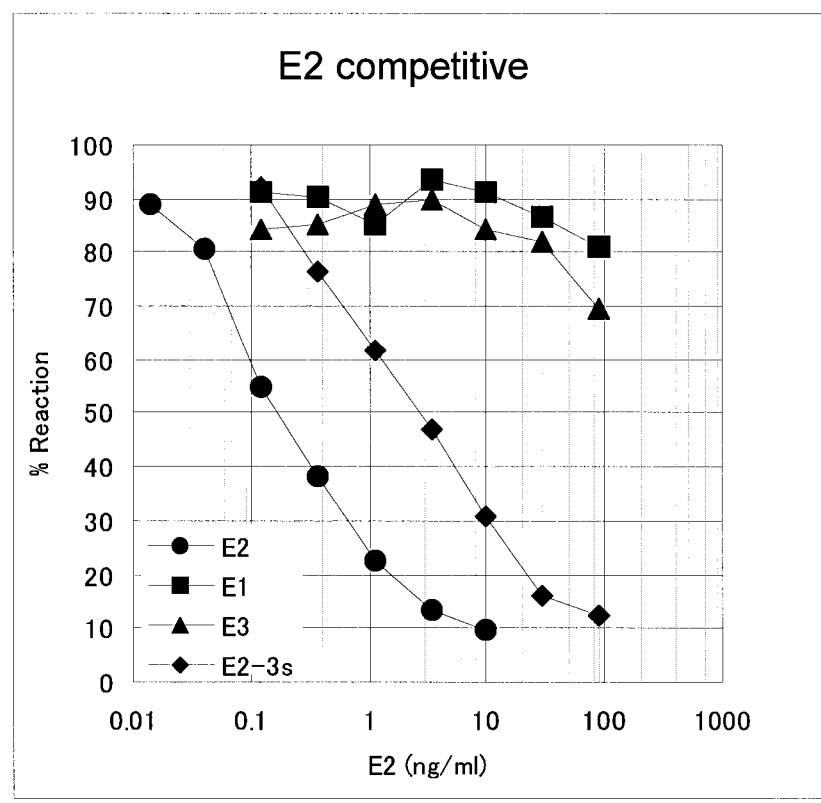
FIG. 9 is a graph illustrating evaluation of a specificity of a solid phase antibody (primary antibody: anti-E2 antibody) by a competitive system.

The primary antibody used in this measurement did not cross-react to E1 and E3 (FIG. 9), but exhibited the cross-reactivity of about 10% to E2-3 sulfate (FIG. 9). Therefore, this primary antibody was shown to be not necessarily highly specific for E2.

(17-2) Improvement of Specificity in Measurement by Sandwich Method (1)

It was evaluated whether it was possible or not to improve the measurement specific for E2 compared to in vivo analogous substances thereto by using the antibody of the present invention.

(A) Method (i) Immobilization of Primary Antibody

The anti-E2 antibody [the same as one used in (17-1) above] was immobilized by the following procedure.

The anti-E2 antibody (2.5 µg/mL) was added to NUNC POLYSORP (96 well plate for ELISA) and incubated overnight.

The plate to which the anti-E2 antibody had been immobilized was blocked with 5% skim milk (37° C., one hour).

(ii) ELISA

ELISA was performed by the following procedure.

The antigen: E2 (diluted at 3n from 2 ng/mL) and analogous antigens: E1, E3, E2-3s (diluted at 3n from 54 ng/mL) were prepared.

The antigen or the analogous antigen (each 50 µL) and a secondary antibody (chicken-derived E2/anti-E2 antibody complex antibody (clone 2-1): 50 µL) were added to the immobilized plate.

The immobilized plate was incubated at 37° C. for one hour.

The immobilized plate was washed three times with PBS/Tween 20 (0.05%).

The anti-chicken IgM/HRP was added to the immobilized plate to perform a secondary reaction.

The immobilized plate was washed three times with PBS/Tween 20 (0.05%).

A color was developed with TMB (3,3',5,5'-tetramethylbenzidine, and the absorbance was measured.

(B) Results

Figure 10:
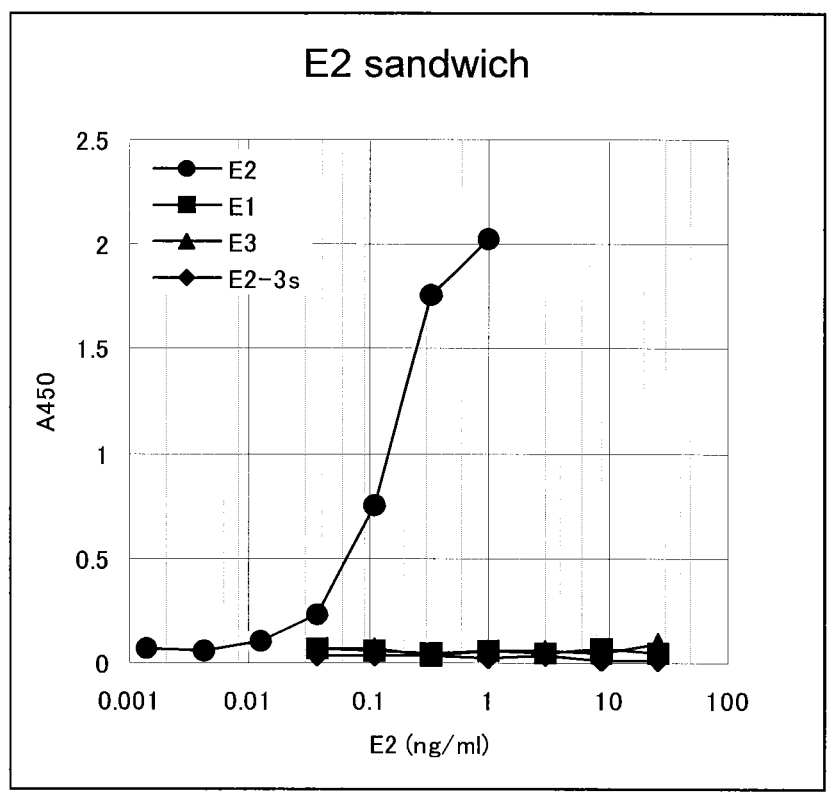
FIG. 10 is a graph illustrating improvement of the specificity in the measurement of E2 by a sandwich method.

The antibody of the present invention could discriminate the "complex of E2 and the primary antibody" from the "complex of E2-3 sulfate and the primary antibody" (FIG. 10). That is, the antibody of the present invention is thought to specifically recognize the presence or the absence of the sulfate group at position 3 of E2 in the complex of E2 and the primary antibody. Therefore, it was shown that the measurement specific for E2 to the in vivo analogous substances could be improved by the use of the antibody of the present invention.

(17-3) Improvement of Specificity in Measurement by Sandwich Method (2)

It was evaluated whether it was possible or not to improve the measurement specific for E2 to therapeutic drugs by using the antibody of the present invention.

(A) Method (i) Immobilization of Primary Antibody

The anti-E2 antibody [the same as one used in (17-1) above] was immobilized by the following procedure.

The anti-E2 antibody (2.5 µg/mL) was added to NUNC POLYSORP (96 well plate for ELISA) and incubated overnight.

The plate to which the anti-E2 antibody had been immobilized was blocked with 5% skim milk (37° C., one hour).

(ii) ELISA

The antigen: E2 (diluted at 3n from 2 ng/mL) and E2 analogous therapeutic drugs (100 ng/mL) were prepared. Estromustine and estramustine were used as the E2 analogous therapeutic drugs.

The antigen or the analogous antigen (each 50 µL) and the secondary antibody (chicken-derived E2/anti-E2 antibody complex antibody (clone 2-1): 50 µL) were added to the immobilized plate.

The immobilized plate was incubated at 37° C. for one hour.

The immobilized plate was washed three times with PBS/Tween 20 (0.05%).

The anti-chicken IgM/HRP was added to the immobilized plate to perform a secondary reaction.

The immobilized plate was washed three times with PBS/Tween 20 (0.05%).

A color was developed with TMB and the absorbance was measured.

The cross-reactivity (%) to the analogous drug was calculated based on the absorbance when E2 was measured.

(B) Results

The antibody of the present invention could discriminate the "complex of E2 and the primary antibody" from the "complex of E2 analogous therapeutic drug and the primary antibody" (Table 16). Therefore, it was shown that the measurement specific for E2 to the E2 analogous therapeutic drugs could be improved by the use of the antibody of the present invention.

TABLE 16

| | Cross-reactivity (%) | |
|---|---|---|
| | Competitive | Sandwich |
| Estromustine | 12 | 0.2 |
| Estramustine | 100 | 10 |

Competitive: competitive ELISA
Sandwich: sandwich ELISA

Example 18

Specificity of the Antibody of the Present Invention for Complex Comprising 25(OH) Vitamin D2 or D3 and Antibody Thereto (18-1) Evaluation of Specificity of Immobilized Antibody (Primary Antibody) by Competitive Method In order to evaluate of the specificity of the antibody of the present invention, first the specificity of the primary antibody for 25(OH) vitamin D2 was evaluated.

(A) Method (i) Immobilization of Primary Antibody

The anti-25OH vitamin D antibody was immobilized by the following procedure.

The anti-25OH vitamin D antibody (1 µg/mL) was added to NUNC MAXISORP (96 well plate for ELISA) and incubated at 37° C. for one hour.

The plate to which the anti-25OH vitamin D antibody had been immobilized was blocked with 1% BSA/PBS (37° C., one hour).

(ii) ELISA

The antigen: 25OH vitamin D3 (diluted at 3n from 111 ng/mL) and analogous antigens: 25OH vitamin D2, 1,25(OH)$_2$ vitamin D3 and 1,25(OH)$_2$ vitamin D2 (diluted at 3n from 111 ng/mL) were prepared.

A labeled antigen: a fusion body of 25OH vitamin D3/ALP at position 3 (20 ng/mL) was prepared.

The antigen or the analogous antigen (each 50 μL) and the labeled antigen (50 μL) were added to the immobilized plate.

The immobilized plate was incubated at 37° C. for one hour.

The immobilized plate was washed three times with PBS/Tween 20 (0.05%).

A color was developed with pNPP and the absorbance was measured.

A reaction in the absence of the antigen or the analogous antigen was made 100%, and an inhibitory rate (% reaction) was calculated when the antigen or the analogous antigen was added at each concentration.

(B) Results

Figure 11:
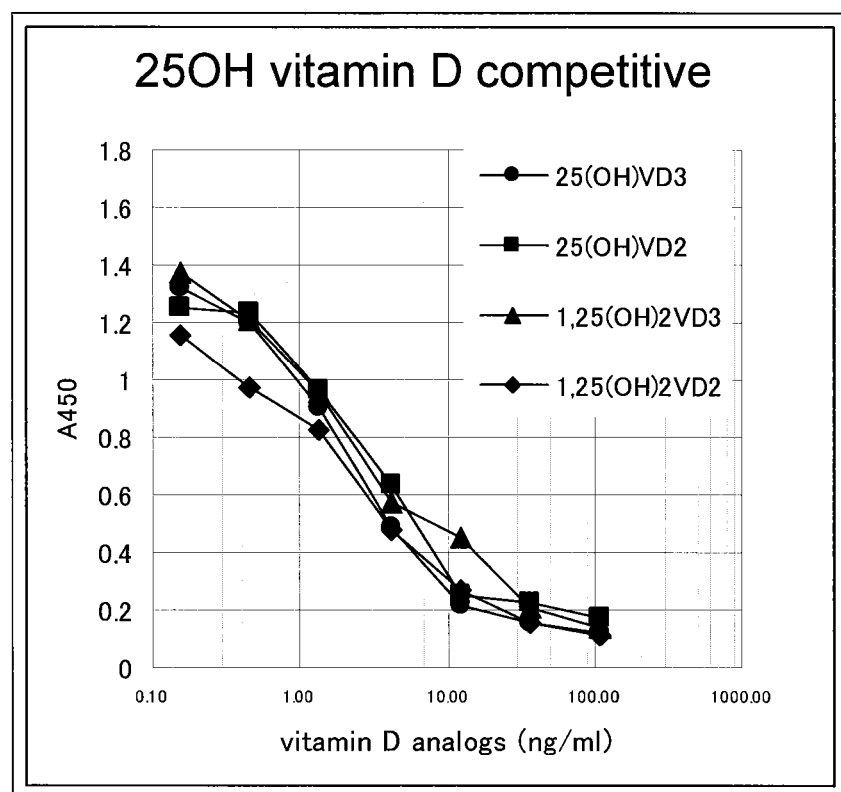
FIG. 11 is a graph illustrating evaluation of the specificity of a solid phase antibody (primary antibody: anti-25OH vitamin D2 antibody) by a competitive system.

The primary antibody used in this measurement reacted to 25(OH) vitamin D2, 25(OH) vitamin D3, 1,25(OH)$_2$ vitamin D2 and 1,25(OH)$_2$ vitamin D3 at similar levels (FIG. 11). Therefore, this primary antibody was shown to have the low specificity for the particular vitamin D.

(18-2) Improvement of Specificity in Measurement by Sandwich Method

It was evaluated whether it was possible or not to improve the measurement specific for the particular vitamin D to in vivo analogous substances thereto by using the antibody of the present invention.

(A) Method (i) Immobilization of Primary Antibody

The anti-25OH vitamin D antibody (the same as one used in (18-1) above) was immobilized by the following procedure.

The anti-25OH vitamin D antibody (1 μg/mL) was added to NUNC MAXISORP (96 well plate for ELISA) and incubated at 37° C. for one hour.

The plate to which the anti-25OH vitamin D antibody had been immobilized was blocked with 1% BSA/PBS (37° C., one hour).

(ii) ELISA

The antigen: 25OH vitamin D3 (diluted at 5n from 370 ng/mL) and the analogous antigens: 25(OH) vitamin D2 (diluted at 5n from 370 ng/mL), and 1,25(OH)$_2$ vitamin D3 and 1,25(OH)$_2$ vitamin D2 (diluted at 5n from 37000 ng/mL) were prepared.

The antigen or the analogous antigen (each 50 μL) was added to the immobilized plate.

The immobilized plate was washed three times with PBS/Tween 20 (0.05%).

The secondary antibody (chicken-derived 25(OH) vitamin D/anti-25OH vitamin D complex antibody, 50 μL) was added to the immobilized plate.

The immobilized plate was incubated at 37° C. for one hour.

The immobilized plate was washed three times with PBS/Tween 20 (0.05%).

The anti-chicken IgG antibody/streptavidin (50 μL) was added to the immobilized plate.

The immobilized plate was incubated at 37° C. for one hour.

The immobilized plate was washed three times with PBS/Tween 20 (0.05%).

Streptavidin/HRP (horseradish peroxidase) (50 μL) was added to the immobilized plate.

The immobilized plate was incubated at 37° C. for one hour.

A color was developed with TMB and the absorbance was measured.

(B) Results

Figure 12:
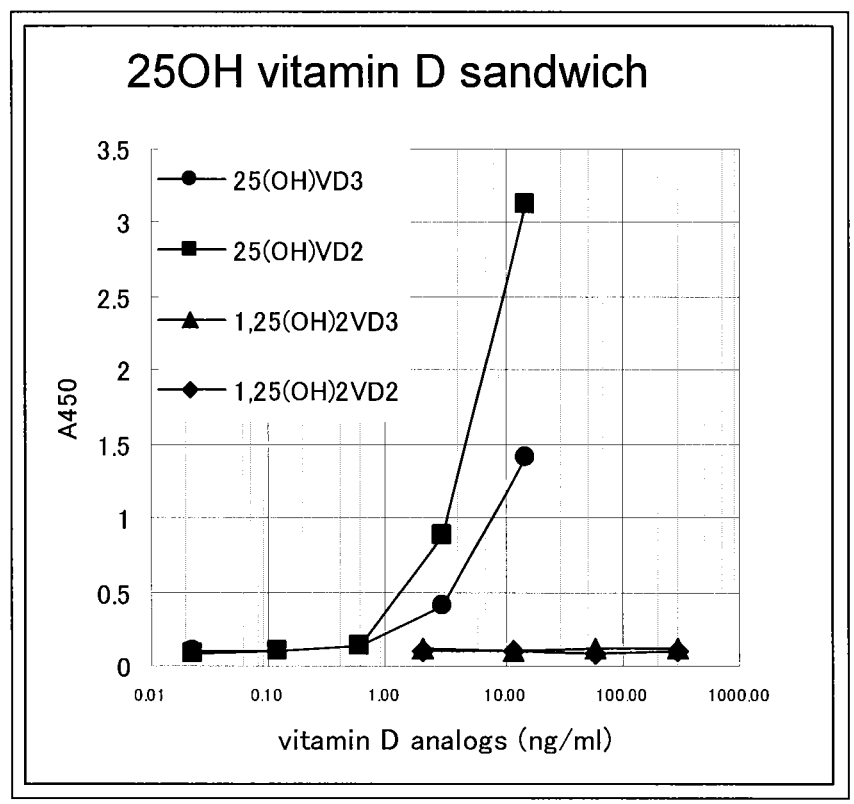
FIG. 12 is a graph illustrating improvement of the specificity in the measurement of anti-25OH vitamin D2 and D3 by a sandwich method

The antibody of the present invention could discriminate the "complex of 25OH vitamin D2 or D3 and the primary antibody" from the "complex of 1,25(OH)$_2$ vitamin D2 or D3 and the primary antibody" (FIG. 12). That is, the antibody of the present invention is thought to specifically recognize the presence of an OH group at position 1 of 1,25(OH)$_2$ vitamin D2 or D3 in the complex of 1,25(OH)$_2$ vitamin D2 or D3 and the primary antibody. Therefore, it was shown that the measurement specific for 1,25(OH)$_2$ vitamin D2 and D3 to the in vivo analogous substances was improved by the use of the antibody of the present invention.

The invention claimed is:

1. An isolated full-length antibody capable of specifically binding to an affinity complex,
   wherein the antibody has a variable region of a chicken IgM,
   wherein the affinity complex comprises a small substance and an antibody specifically binding to the small substance, and
   wherein the small substance is any one of
   25OH vitamin D3; or
   25OH vitamin D2;
   wherein binding rate of the full-length antibody to an affinity complex comprising 1,25(OH)$_2$ vitamin D3 or 1,25(OH)$_2$ vitamin D2 and an anti-25OH vitamin D3 antibody or an anti-25OH vitamin D2 antibody is 10% or less as compared to 100% binding rate of the full-length antibody to said affinity complex comprising the small substance and the antibody specifically binding to the small substance.

2. The isolated full-length antibody according to claim 1, wherein the antibody is produced by a method comprising culturing a DT40 cell having an ability to produce the antibody capable of specifically binding to the affinity complex, to obtain the isolated full-length antibody.

3. The isolated full-length antibody according to claim 1, wherein the isolated full-length antibody specifically binds to an affinity complex comprising the small substance 25OH vitamin D3 and an anti-25OH vitamin D3 antibody and wherein the binding rate of the isolated full-length antibody to an affinity complex comprising 1,25(OH)$_2$ vitamin D3 and an anti-25OH vitamin D3 antibody or an anti-25OH vitamin D2 antibody or an affinity complex comprising 1,25(OH)$_2$ vitamin D2 and the anti-25OH vitamin D3 antibody or the anti-25OH vitamin D2 antibody is 10% or less as compared to 100% binding rate of the isolated full-length antibody specifically binding to the affinity complex comprising the 25OH vitamin D3 and the anti-25OH vitamin D3 antibody.

4. The isolated full-length antibody according to claim 1, wherein the isolated full-length antibody specifically binds to an affinity complex comprising the small substance 25OH vitamin D2 and an anti-25OH vitamin D2 antibody and wherein the binding rate of the isolated full-length antibody to an affinity complex comprising 1,25(OH)$_2$ vitamin D3 and an anti-25OH vitamin D3 antibody or an anti-25OH vitamin D2 antibody or an affinity complex comprising 1,25(OH)$_2$ vitamin D2 and the anti-25OH vitamin D3 antibody or the anti-25OH vitamin D2 antibody is 10% or less as compared to 100% binding rate of the isolated full-length antibody specifically binding to the affinity complex comprising the 25OH vitamin D2 and the anti-25OH vitamin D2 antibody.

* * * * *

SEQUENCE LISTING

```
<160> NUMBER OF SEQ ID NOS: 12

<210> SEQ ID NO 1
<211> LENGTH: 43
<212> TYPE: DNA
<213> ORGANISM: Artificial Sequence
<220> FEATURE:
<223> OTHER INFORMATION: Primer A

<400> SEQUENCE: 1
cagcagcaga agcttccacc atgagcccac tcgtctcctc cct            43

<210> SEQ ID NO 2
<211> LENGTH: 31
<212> TYPE: DNA
<213> ORGANISM: Artificial Sequence
<220> FEATURE:
<223> OTHER INFORMATION: Primer B

<400> SEQUENCE: 2
```
tcgttttggc ggaggagacg atgacttcgg t							31

<210> SEQ ID NO 3
<211> LENGTH: 30
<212> TYPE: DNA
<213> ORGANISM: Artificial Sequence
<220> FEATURE:
<223> OTHER INFORMATION: Primer C

<400> SEQUENCE: 3
cgtctcctcc gccaaaacga cacccccatc							30

<210> SEQ ID NO 4
<211> LENGTH: 41
<212> TYPE: DNA
<213> ORGANISM: Artificial Sequence
<220> FEATURE:
<223> OTHER INFORMATION: Primer D

<400> SEQUENCE: 4
cagcagcagg cggccgctca tttaccagga gagtgggaga g						41

<210> SEQ ID NO 5
<211> LENGTH: 44
<212> TYPE: DNA
<213> ORGANISM: Artificial Sequence
<220> FEATURE:
<223> OTHER INFORMATION: Primer E

<400> SEQUENCE: 5
cagcagcaga agcttccacc atggcctggg ctcctctcct cctg					44

<210> SEQ ID NO 6
<211> LENGTH: 31
<212> TYPE: DNA
<213> ORGANISM: Artificial Sequence
<220> FEATURE:
<223> OTHER INFORMATION: Primer F

<400> SEQUENCE: 6
cagcatcagc acctaggacg gtcagggttg t						31

<210> SEQ ID NO 7
<211> LENGTH: 30
<212> TYPE: DNA
<213> ORGANISM: Artificial Sequence
<220> FEATURE:
<223> OTHER INFORMATION: Primer G

<400> SEQUENCE: 7
cgtcctaggt gctgatgctg caccaactgt							30

<210> SEQ ID NO 8
<211> LENGTH: 41
<212> TYPE: DNA
<213> ORGANISM: Artificial Sequence
<220> FEATURE:
<223> OTHER INFORMATION: Primer H

<400> SEQUENCE: 8
cagcagcagg cggccgccta acactcattc ctgttgaagc t						41

<210> SEQ ID NO 9
<211> LENGTH: 43
<212> TYPE: DNA
<213> ORGANISM: Artificial Sequence

```
-continued

<220> FEATURE:
<223> OTHER INFORMATION: Primer I

<400> SEQUENCE: 9
cagcagcagg ctagcccacc atgagcccac tcgtctcctc cct                    43

<210> SEQ ID NO 10
<211> LENGTH: 42
<212> TYPE: DNA
<213> ORGANISM: Artificial Sequence
<220> FEATURE:
<223> OTHER INFORMATION: Primer J

<400> SEQUENCE: 10
acaaccacaa tccctgggca cgggaatcgg gggacctggg tt                     42

<210> SEQ ID NO 11
<211> LENGTH: 42
<212> TYPE: DNA
<213> ORGANISM: Artificial Sequence
<220> FEATURE:
<223> OTHER INFORMATION: Primer K

<400> SEQUENCE: 11
aacccaggtc ccccgattcc cgtgcccagg gattgtggtt gt                     42

<210> SEQ ID NO 12
<211> LENGTH: 41
<212> TYPE: DNA
<213> ORGANISM: Artificial Sequence
<220> FEATURE:
<223> OTHER INFORMATION: Primer L

<400> SEQUENCE: 12
ctgctgctgg cggccgctta gcactcggac ctcttcaggg t                      41
```